US009393192B2

(12) United States Patent
Yam et al.

(10) Patent No.: US 9,393,192 B2
(45) Date of Patent: Jul. 19, 2016

(54) METHODS AND DOSAGE FORMS FOR CONTROLLED DELIVERY OF PALIPERIDONE AND RISPERIDONE

(75) Inventors: Nyomi V. Yam, Sunnyvale, CA (US); Iran Reyes, San Jose, CA (US); Nipun Davar, Fremont, CA (US); Atul D. Ayer, Palo Alto, CA (US); Julie Lee, Sunnyvale, CA (US); Sonya Seroff, San Jose, CA (US); Suneel K. Gupta, Sunnyvale, CA (US); Gayatri Sathyan, San Jose, CA (US)

(73) Assignee: ALZA CORPORATION

( * ) Notice: Subject to any disclaimer, the term of this patent is extended or adjusted under 35 U.S.C. 154(b) by 825 days.

(21) Appl. No.: 12/428,422

(22) Filed: Apr. 22, 2009

(65) Prior Publication Data
US 2009/0202631 A1    Aug. 13, 2009

Related U.S. Application Data

(63) Continuation of application No. 11/051,165, filed on Feb. 4, 2005, now abandoned, which is a continuation-in-part of application No. 10/629,211, filed on Jul. 28, 2003, now abandoned.

(60) Provisional application No. 60/399,590, filed on Jul. 29, 2002, provisional application No. 60/406,005, filed on Aug. 26, 2002.

(51) Int. Cl.
*A61K 9/22* (2006.01)
*A61K 9/00* (2006.01)
*A61K 31/506* (2006.01)
*A61K 31/519* (2006.01)

(52) U.S. Cl.
CPC ............ *A61K 9/0004* (2013.01); *A61K 31/506* (2013.01); *A61K 31/519* (2013.01)

(58) Field of Classification Search
USPC .......................... 424/464, 468, 474; 544/282
See application file for complete search history.

(56) References Cited

U.S. PATENT DOCUMENTS

| | | |
|---|---|---|
| 2,507,631 A | 5/1950 | Hartmann et al. |
| 2,648,609 A | 8/1953 | Wuster |
| 2,668,162 A | 2/1954 | Lowe |
| 2,676,945 A | 4/1954 | Higgins |
| 2,707,154 A | 4/1955 | Lehmann et al. |
| 2,738,303 A | 3/1956 | Blythe |
| 2,798,053 A | 4/1957 | Brown |
| 2,799,241 A | 7/1957 | Wurster |
| 2,909,462 A | 10/1959 | Warfield et al. |
| 2,957,880 A | 10/1960 | Rometsch |
| 2,996,431 A | 8/1961 | Barry |
| 3,133,132 A | 5/1964 | Loeb et al. |
| 3,139,383 A | 6/1964 | Neville, Jr. |
| 3,173,876 A | 3/1965 | Jackson |
| 3,276,586 A | 10/1966 | Rosean |
| 3,541,005 A | 11/1970 | Strathmann et al. |
| 3,541,006 A | 11/1970 | Bixler et al. |
| 3,546,142 A | 12/1970 | Michaels et al. |
| 3,573,936 A | 4/1971 | Karchmar |
| 3,598,122 A | 8/1971 | Zaffaroni et al. |
| 3,598,123 A | 8/1971 | Zaffaroni et al. |
| 3,625,214 A | 12/1971 | Higuch |
| 3,637,772 A | 1/1972 | Kaui et al. |
| 3,773,919 A | 11/1973 | Boswell et al. |
| 3,811,444 A | 5/1974 | Heller et al. |
| 3,825,068 A | 7/1974 | Norton et al. |
| 3,845,770 A | 11/1974 | Theeuwes et al. |
| 3,865,108 A | 2/1975 | Hartop |
| 3,916,899 A | 11/1975 | Theeuwes et al. |
| 3,962,414 A | 6/1976 | Michaels |
| 3,992,518 A | 11/1976 | Chien et al. |
| 3,995,631 A | 12/1976 | Higuchi |
| 4,002,173 A | 1/1977 | Manning et al. |
| 4,008,719 A | 2/1977 | Theeuwes et al. |
| 4,036,228 A | 7/1977 | Theeuwes |
| 4,038,434 A | 7/1977 | Young |
| 4,063,064 A | 12/1977 | Saunders et al. |

(Continued)

FOREIGN PATENT DOCUMENTS

| | | |
|---|---|---|
| BE | 6753579 | 6/2004 |
| CA | 1169090 | 6/1984 |

(Continued)

OTHER PUBLICATIONS

Fenton, Caroline; Scott, Lesley J., Risperidone: A Rev1ew of its Use in the Treatment of Bipolar Mania: 2005: ADIS Data Information BV: CNS Drugs vol. 15. No. 5. pp. 429-444.

Love. Raymond C. Strategies for increasing treatment compliance: The role of long-acting antipsychotics: 2002: American Society of Health-System Pharmacists: American Journal of Health-Systems Pharmacists. vol. 19. Suppl. 8. pp. S10-S15.

(Continued)

*Primary Examiner* — Ali Soroush
(74) *Attorney, Agent, or Firm* — Hal B. Woodrow

(57) ABSTRACT

Dosage forms and methods for providing a substantially ascending rate of release of paliperidone or risperidone are provided. The sustained release dosage forms provide therapeutically effective average steady-state plasma paliperidone or risperidone concentrations when administered once per day. This once-a-day dosing regimen results in only one peak plasma paliperidone or risperidone concentration occurrence in each 24 hour period. In addition, the peak plasma paliperidone or risperidone concentration occurs at a later time following dose administration and exhibits a lesser magnitude than the peak plasma paliperidone or risperidone concentration that occurs following administration of paliperidone or risperidone in an immediate-release dosage form.

14 Claims, 7 Drawing Sheets

(56) References Cited

U.S. PATENT DOCUMENTS

| | | |
|---|---|---|
| 4,066,747 A | 1/1978 | Capozza |
| 4,070,347 A | 1/1978 | Schmitt |
| 4,077,407 A | 3/1978 | Theeuwes et al. |
| 4,079,038 A | 3/1978 | Choi et al. |
| 4,083,949 A | 4/1978 | Benedikt |
| 4,088,864 A | 5/1978 | Theeuwes |
| 4,093,709 A | 6/1978 | Choi et al. |
| 4,111,201 A | 9/1978 | Theeuwes |
| 4,111,202 A | 9/1978 | Theeuwes |
| 4,137,300 A | 1/1979 | Sheth et al. |
| 4,160,020 A | 7/1979 | Ayer et al. |
| 4,186,465 A | 2/1980 | Manning |
| 4,200,098 A | 4/1980 | Ayer et al. |
| 4,207,893 A | 6/1980 | Michaels |
| 4,259,323 A | 3/1981 | Ranucci |
| 4,285,987 A | 8/1981 | Ayer et al. |
| 4,327,725 A | 5/1982 | Cortese et al. |
| 4,327,728 A | 5/1982 | Elias |
| 4,352,811 A | 10/1982 | Strupczewski et al. |
| 4,434,153 A | 2/1984 | Urquhart et al. |
| 4,449,983 A | 5/1984 | Cortese et al. |
| 4,458,076 A | 7/1984 | Strupczewski et al. |
| 4,519,801 A | 5/1985 | Edgren |
| 4,559,237 A | 12/1985 | Meier et al. |
| 4,578,075 A | 3/1986 | Urquhart et al. |
| 4,612,008 A | 9/1986 | Wong et al. |
| 4,627,850 A | 12/1986 | Deters et al. |
| 4,663,148 A | 5/1987 | Eckenhoff et al. |
| 4,681,583 A | 7/1987 | Urquhart et al. |
| 4,721,613 A | 1/1988 | Urquhart et al. |
| 4,752,470 A | 6/1988 | Mehta |
| 4,783,337 A | 11/1988 | Wong et al. |
| 4,803,251 A | 2/1989 | Goode et al. |
| 4,804,663 A | 2/1989 | Kennis et al. |
| 4,804,665 A | 2/1989 | Goto et al. |
| 4,814,181 A | 3/1989 | Jordan et al. |
| 4,824,675 A | 4/1989 | Wong et al. |
| 4,842,867 A | 6/1989 | Ayer et al. |
| 4,853,229 A | 8/1989 | Theeuwes |
| 4,855,370 A | 8/1989 | Chirillo et al. |
| 4,859,469 A | 8/1989 | Baudier et al. |
| 4,888,168 A | 12/1989 | Potts et al. |
| 4,892,778 A | 1/1990 | Theeuwes et al. |
| 4,915,949 A | 4/1990 | Wong et al. |
| 4,931,285 A | 6/1990 | Edgren et al. |
| 4,940,465 A | 7/1990 | Theeuwes et al. |
| 4,957,494 A | 9/1990 | Wong et al. |
| 4,961,932 A | 10/1990 | Theeuwes |
| 4,980,170 A | 12/1990 | Schneider et al. |
| 5,006,346 A | 4/1991 | Edgren et al. |
| 5,007,790 A | 4/1991 | Shell |
| 5,017,381 A | 5/1991 | Maruyama et al. |
| 5,019,397 A | 5/1991 | Wong et al. |
| 5,023,088 A | 6/1991 | Wong et al. |
| 5,024,842 A | 6/1991 | Edgren et al. |
| 5,030,456 A | 7/1991 | Ayer et al. |
| 5,082,655 A | 1/1992 | Snipes et al. |
| 5,082,668 A | 1/1992 | Wong et al. |
| 5,089,270 A | 2/1992 | Hampton et al. |
| 5,091,190 A | 2/1992 | Kuczynski et al. |
| 5,094,786 A | 3/1992 | Nagashima et al. |
| 5,110,597 A | 5/1992 | Wong et al. |
| 5,112,817 A | 5/1992 | Fukazawa et al. |
| 5,126,142 A | 6/1992 | Ayer et al. |
| 5,156,850 A | 10/1992 | Wong et al. |
| 5,158,952 A | 10/1992 | Janssen et al. |
| 5,160,743 A | 11/1992 | Edgren et al. |
| 5,169,638 A | 12/1992 | Dennis et al. |
| 5,178,866 A | 1/1993 | Wright et al. |
| 5,190,765 A | 3/1993 | Jao et al. |
| 5,236,689 A | 8/1993 | Wong et al. |
| 5,240,713 A | 8/1993 | Ayer |
| 5,252,338 A | 10/1993 | Jao et al. |
| 5,262,171 A | 11/1993 | Login et al. |
| 5,294,770 A | 3/1994 | Riddle et al. |
| 5,324,280 A | 6/1994 | Wong et al. |
| 5,330,762 A | 7/1994 | Ayer et al. |
| 5,340,590 A | 8/1994 | Wong et al. |
| 5,346,304 A | 9/1994 | Kleinhans |
| 5,391,381 A | 2/1995 | Wong et al. |
| 5,391,657 A | 2/1995 | Song et al. |
| 5,399,828 A | 3/1995 | Riddle et al. |
| 5,405,922 A | 4/1995 | Dechellis et al. |
| 5,422,831 A | 6/1995 | Misra et al. |
| 5,436,304 A | 7/1995 | Griffin et al. |
| 5,453,425 A | 9/1995 | Francois et al. |
| 5,464,631 A | 11/1995 | Hoover et al. |
| 5,484,607 A | 1/1996 | Horacek |
| 5,512,593 A | 4/1996 | Dante |
| 5,534,263 A | 7/1996 | Wong et al. |
| 5,536,507 A | 7/1996 | Abramowitz et al. |
| 5,541,270 A | 7/1996 | Chinh et al. |
| 5,558,231 A | 9/1996 | Weier |
| 5,614,578 A | 3/1997 | Dong et al. |
| 5,620,705 A | 4/1997 | Dong et al. |
| 5,633,011 A | 5/1997 | Dong et al. |
| 5,643,909 A | 7/1997 | Pfister et al. |
| 5,648,581 A | 7/1997 | Kubo et al. |
| 5,650,173 A | 7/1997 | Ramstock et al. |
| 5,654,008 A | 8/1997 | Herbert et al. |
| 5,656,299 A | 8/1997 | Kino et al. |
| 5,660,861 A | 8/1997 | Jao et al. |
| 5,667,804 A | 9/1997 | Wong et al. |
| 5,692,477 A | 12/1997 | Berger et al. |
| 5,707,663 A | 1/1998 | Ayer et al. |
| 5,718,700 A | 2/1998 | Edgren et al. |
| 5,733,510 A | 3/1998 | Chinh et al. |
| 5,770,227 A | 6/1998 | Dong et al. |
| 5,770,231 A | 6/1998 | Mesens et al. |
| 5,770,843 A | 6/1998 | Rose et al. |
| 5,785,994 A | 7/1998 | Wong et al. |
| 5,817,321 A | 10/1998 | Alakhov et al. |
| 5,824,338 A | 10/1998 | Jacobs et al. |
| 5,824,638 A | 10/1998 | Burnside et al. |
| 5,837,284 A | 11/1998 | Mehta et al. |
| 5,869,097 A | 2/1999 | Wong et al. |
| 5,871,778 A | 2/1999 | Kino et al. |
| 5,874,090 A | 2/1999 | Baker et al. |
| 5,906,832 A | 5/1999 | Jao et al. |
| 5,938,654 A | 8/1999 | Wong et al. |
| 5,965,168 A | 10/1999 | Mesens et al. |
| 6,001,938 A | 12/1999 | Chinh et al. |
| 6,008,662 A | 12/1999 | Newton et al. |
| 6,020,000 A | 2/2000 | Wong et al. |
| 6,036,973 A | 3/2000 | Guittard et al. |
| 6,077,843 A | 6/2000 | François et al. |
| 6,110,923 A | 8/2000 | Ely |
| 6,124,355 A | 9/2000 | Guittard et al. |
| 6,174,547 B1 | 1/2001 | Dong et al. |
| 6,210,712 B1 | 4/2001 | Edgren et al. |
| 6,245,357 B1 | 6/2001 | Edgren et al. |
| 6,248,363 B1 | 6/2001 | Patel et al. |
| 6,294,192 B1 | 9/2001 | Patel et al. |
| 6,352,721 B1 | 3/2002 | Faour |
| 6,368,626 B1 | 4/2002 | Bhatt et al. |
| 6,368,632 B1 | 4/2002 | Mesens et al. |
| 6,395,727 B1 | 5/2002 | Guadagno et al. |
| 6,419,952 B2 | 7/2002 | Wong et al. |
| 6,491,949 B2 | 12/2002 | Faour et al. |
| 6,500,833 B1 | 12/2002 | Yelle |
| 6,521,255 B2 | 2/2003 | Vergez et al. |
| 6,551,613 B2 | 4/2003 | Dong et al. |
| 6,562,375 B1 | 5/2003 | Sako et al. |
| 6,569,456 B2 | 5/2003 | Faour et al. |
| 6,569,463 B2 | 5/2003 | Patel et al. |
| 6,572,890 B2 | 6/2003 | Faour et al. |
| 6,596,314 B2 | 7/2003 | Wong et al. |
| 6,599,284 B2 | 7/2003 | Faour |
| 6,599,532 B2 | 7/2003 | Faour et al. |
| 6,605,302 B2 | 8/2003 | Faour et al. |
| 6,613,357 B2 | 9/2003 | Faour et al. |
| 6,667,060 B1 | 12/2003 | Vandecruys |
| 6,706,282 B1 | 3/2004 | Cruz |
| 6,753,011 B2 | 6/2004 | Faour |

(56) References Cited

U.S. PATENT DOCUMENTS

| | | | |
|---|---|---|---|
| 6,855,334 | B2 | 2/2005 | Bhatt et al. |
| 6,919,373 | B1 | 7/2005 | Lam et al. |
| 6,930,129 | B2 | 8/2005 | Lam |
| 7,008,641 | B2 | 3/2006 | Faour et al. |
| RE39,069 | E | 4/2006 | Faour et al. |
| 7,147,870 | B2 | 12/2006 | Faour et al. |
| 8,323,691 | B2 | 12/2012 | Geerke et al. |
| 2001/0012847 | A1 | 8/2001 | Lam et al. |
| 2001/0031279 | A1 | 10/2001 | Cruz et al. |
| 2002/0022245 | A1 | 2/2002 | Hebebrand et al. |
| 2002/0035357 | A1 | 3/2002 | Faour et al. |
| 2002/0044960 | A1 | 4/2002 | Cherukuri |
| 2002/0044962 | A1 | 4/2002 | Cherukuri et al. |
| 2002/0047712 | A1 | 4/2002 | Weick et al. |
| 2002/0048600 | A1 | 4/2002 | Bhatt et al. |
| 2002/0051807 | A1 | 5/2002 | Faour et al. |
| 2002/0082245 | A1 | 6/2002 | Yelle |
| 2002/0127196 | A1 | 9/2002 | Avila et al. |
| 2003/0021841 | A1 | 1/2003 | Matharu et al. |
| 2003/0180352 | A1 | 9/2003 | Patel et al. |
| 2003/0185882 | A1 | 10/2003 | Vergez et al. |
| 2003/0228358 | A1 | 12/2003 | Perlman et al. |
| 2004/0091529 | A1 | 5/2004 | Edgren et al. |
| 2004/0092534 | A1 | 5/2004 | Yam et al. |
| 2004/0115262 | A1 | 6/2004 | Jao et al. |
| 2005/0053653 | A1 | 3/2005 | Kidane et al. |
| 2005/0058707 | A1 | 3/2005 | Reyes et al. |
| 2005/0136108 | A1 | 6/2005 | Yam et al. |
| 2005/0208132 | A1 | 9/2005 | Sathyan et al. |
| 2006/0034927 | A1 | 2/2006 | Casadevall et al. |
| 2007/0026067 | A1 | 2/2007 | Yam et al. |
| 2007/0243254 | A1 | 10/2007 | Edgren et al. |

FOREIGN PATENT DOCUMENTS

| | | | |
|---|---|---|---|
| CN | 1352549 | | 6/2002 |
| DE | 2800157 | A1 | 7/1978 |
| EP | 0094123 | A2 | 11/1983 |
| EP | 0212747 | | 4/1987 |
| EP | 0216743 | B1 | 4/1987 |
| EP | 0275444 | | 7/1987 |
| EP | 0251459 | | 1/1988 |
| EP | 0326430 | | 1/1989 |
| EP | 0348808 | B1 | 1/1990 |
| EP | 0378404 | | 7/1990 |
| EP | 0318219 | B1 | 8/1990 |
| EP | 0621032 | B1 | 10/1994 |
| EP | 1027888 | | 8/2000 |
| EP | 0635724 | | 9/2001 |
| EP | 1539115 | | 9/2007 |
| ES | 2050069 | | 12/1994 |
| FR | 2598319 | | 5/1997 |
| FR | 2620025 | | 9/1998 |
| GB | 1113860 | | 12/1965 |
| GB | 2206046 | | 12/1998 |
| GB | 2206047 | | 12/1998 |
| JP | 292733/87 | | 12/1987 |
| JP | 229110/90 | | 9/1990 |
| KR | 10-2002-0031424 | | 5/2002 |
| RU | 2161965 | | 1/2001 |
| WO | 91/03247 | A1 | 3/1991 |
| WO | 92/01445 | A1 | 2/1992 |
| WO | 92/04012 | A1 | 3/1992 |
| WO | WO 92/04011 | | 3/1992 |
| WO | 92/18102 | A1 | 10/1992 |
| WO | 93/05769 | A1 | 4/1993 |
| WO | WO 94/25460 | | 11/1994 |
| WO | 95/06460 | A1 | 3/1995 |
| WO | WO 95/13814 | | 5/1995 |
| WO | 95/19174 | A1 | 7/1995 |
| WO | 95/20946 | A1 | 8/1995 |
| WO | 97/02017 | A1 | 1/1997 |
| WO | 97/44039 | A1 | 11/1997 |
| WO | WO 97/41837 | | 11/1997 |
| WO | 96/31201 | A1 | 2/1998 |
| WO | 98/06380 | A2 | 2/1998 |
| WO | 98/06380 | A3 | 2/1998 |
| WO | 98/14168 | A2 | 4/1998 |
| WO | 98/14168 | A3 | 4/1998 |
| WO | 98/23263 | A1 | 6/1998 |
| WO | 99/40943 | A1 | 8/1999 |
| WO | 99/44581 | A2 | 9/1999 |
| WO | WO 99/59590 | | 11/1999 |
| WO | 99/62496 | A1 | 12/1999 |
| WO | WO 99/62496 | * | 12/1999 |
| WO | 00/00179 | A1 | 1/2000 |
| WO | 00/25753 | A2 | 5/2000 |
| WO | 00/25790 | A1 | 5/2000 |
| WO | WO-00/25790 | * | 5/2000 |
| WO | 00/35419 | A2 | 6/2000 |
| WO | 00/48607 | A1 | 8/2000 |
| WO | WO 00/54764 | | 9/2000 |
| WO | 00/59477 | A1 | 10/2000 |
| WO | WO-00/59477 | * | 10/2000 |
| WO | 01/12155 | A1 | 2/2001 |
| WO | 01/19337 | | 3/2001 |
| WO | 01/34120 | A1 | 5/2001 |
| WO | 01/37813 | A2 | 5/2001 |
| WO | 01/37813 | A3 | 5/2001 |
| WO | 01/52819 | A1 | 7/2001 |
| WO | WO 02/12200 | | 2/2002 |
| WO | WO 02/087512 | | 11/2002 |
| WO | 03/002151 | A1 | 1/2003 |
| WO | 03/004009 | A1 | 2/2003 |
| WO | 03/011204 | A2 | 2/2003 |
| WO | 03/011205 | A2 | 2/2003 |
| WO | 03/039519 | A2 | 5/2003 |
| WO | 03/063833 | A1 | 8/2003 |
| WO | 03/084511 | A1 | 10/2003 |
| WO | 2004/002447 | A2 | 1/2004 |
| WO | 2004/010981 | A1 | 2/2004 |
| WO | WO 2004/094414 | | 11/2004 |
| WO | 2004/010970 | A1 | 2/2005 |
| WO | 2005/016306 | A2 | 2/2005 |
| WO | 2005/020959 | A2 | 3/2005 |
| WO | WO 2005/041924 | | 5/2005 |
| WO | 2005/048981 | A1 | 6/2005 |
| WO | 2005/063206 | A1 | 7/2005 |
| WO | 2006/017537 | A1 | 2/2006 |
| WO | WO 2006/085856 | | 8/2006 |
| WO | 2007/016388 | A2 | 2/2007 |
| WO | 2007/044234 | A1 | 4/2007 |
| WO | WO 2007/050377 | | 5/2007 |

OTHER PUBLICATIONS

Santus et al., 1995, Elsevier, Journal of Controlled Release, vol. 35, pp. 1-21.

Karlsson et al., "Pharmacokinetics and dopamine D2 and serotonin 5-HT2A receptor occupancy of paliperidone in healthy subjects", P.1.053, European Neuropsychopharmacology, Elsevier Science Publishers BV, Amsterdam, NL, vol. 15, 2005, p. S386.

Harrison et al. "Long-Acting Risperidone: A review of Its Use in Schizophrenia." CNS Drugs, vol. 18, No. 2, 2004, pp. 113-132.

"The first atypical agent in depot form opens new perspectives in the treatment of schizophrenia" Nervenheilkunde 2003 Germany, vol. 22, No. 9, 2003, p. 95 [See attached translation].

Frigerio, A. et al., Extract from "Spectrum der Wissenschaft, Spezial 6: Pharmaforschung", Nov. 1997, pp. 72-79 entitled "Neue Arzneimittelformen" [See attached translation].

Bass DM et al., Original Research Article, "Gastrointestinal Safety of an Extended-Release, Nondeformable, Oral Dosage Form (OROS®)", Drug Safety 2002: 25(14): pp. 1021-1033.

Conley et al., "A Randomized Double-Blind Study of Risperidone and Olanzapine in the Treatment of Schizophrenia or Schizoaffective Disorder," Am J Psychiatry 158:5 (May 2001).

Eerdekens et al., "Pharmacokinetics and tolerability of long-acting risperidone in schizophrenia," Schizophrenia Research 70:91-100 (2004).

Hirschfeld et al., "Rapid Antimanic Effect of Risperidone Monotherapy: A 3-Week Multicenter, Double-Blind, Placebo-Controlled Trial," Am J Psychiatry 161:6 (Jun. 2004).

(56) References Cited

OTHER PUBLICATIONS

Kapur et al., "Clinical and Theoretical Implications of 5-HT2 and D2 Receptor Occupancy of Clozapine, Risperidone, and Olanzapine in Schizophrenia," Am J Psychiatry 156:2 (Feb. 1999).
Kelsoe et al., "Possible Locus for Bipolar Disorder Near the Dopamine Transporter on Chromosome 5," Am J Med Genetics (Neuropsychiatric Genetics) 67:533-540 (1996).
Marder et al., "Maintenance Treatment of Schizophrenia With Risperidone or Haloperidol: 2-Year Outcomes," Am J Psychiatry 160:8 (Aug. 2003).
Richelson et al., "Binding of antipsychotic drugs to human brain receptors: Focus on newer generation compounds,"Life Sciences 68:29-39 (2000).
Schotte et al., "Receptor Binding Profile of Risperidone," Acta psychiat. Belg. 98(Suppl. 1):64-75 (1998).
Schotte et al., "Risperidone compared with new and reference antipsychotics drugs: in vitro and in vivo receptor binding" Psychopharmacology 124:57-73 (1996).
The Carlat Psychiatry Report, "An unbiased monthly covering all things psychiatric," vol. 5, No. 3, Mar. 2007, p. 1-8.
Yatham, "Acute and the maintenance treatment of bipolar mania: the role of atypical antipsychotics," Bipolar Disorders 5 (Suppl. 2):7-19 (2003).
Zapata et al., "D3 receptor ligands modulate extracellular dopamine clearance in the nucleus accumbens," J Neurochemistry 81:1035-42 (2002).
Rouse, B.P., Jr., Encyclopedia of Polymer Science and Technology, 3: 325-354, Interscience Publishers, NY, 1964, "Cellulose Esters, Organic".
Takenaka et al., Yakuhaku Zasshi, 115(10): 773-789, 1995, "Discovery and Development of Tamsulosin Hydrochloride, a new $\alpha_1$-Adrenoceptor Antagonist".
Van Nostrand Reinhold Encyclopedia of Chemistry, Douglas M. Considine, Editor, Van Nostrand Reinhold Co., $4^{th}$ Ed., pp. 644-645, 1984.
Achari, Ramanuj et al., J Clin Pharmocol, 38;545-553, 1998. "effects of Oral Intravenous terazosin and Head-up Tilt on blood Pressure Response in Patients with Hypertension".
Alavart, R., Ann Cardiol Angeiol (Paris), 38(9); 599-601, 1989. "ALPRESS® Comprimes Osmotiques: Une Avance Majeure Dans l'Abord de l'Hypertendu".
Bernier, Pablo A., et al., Infections in Urology, 118-125, 1997. "Recent Trials for Medical Treatment of Benign Prostatic Hyperplasia".
Borison, Richard L., et al., *Psycopharmacology Bulletin*, 30(2): 193-197, 1994. "Pharmacokinetics of Risperidone in Chronic Schizophrenic Patients".
Buzelin, J.M., et al., British Journal of Urology, 79, 898-906, 1997, "Clinical uroselectivity: evidence from patients treated with slow-release alfuzosin for symptomatic benign prostatic obstruction".
Florence, Alexander T. et al., Drug Safety, 10(3):233-266, 1994. "Novel Oral Drug Formulations: Their Potential in Modulating Adverse Effects".
*Encyclopedia of Polymer Science and Technology*, 3:325-354, Interscience Publishers, NY, 1964. "Cellulose Esters, Organic".
Giancarlo Santus & Richard W. Baker, "Osmotic drug delivery: a review of the patent literature," *Journal of Controlled Release*, 35:1-21, 1995.
*Van Nostrand Reinhold Encyclopedia of Chemistry*, Douglas M Considine, Editor, Van Nostrand Reinhold Co., $4^{th}$ Ed., pp. 644-645, 1984.
Hixon, Larry et al., *Chemical Engineering*, 94-103, Nov. 1990. "Sizing Materials by Crushing and Grinding".
Huang, May-Lynn, et al., *Clin Pharmocol Ther*, 54:257-268, 1993 "Pharmacokinetics of the novel antipsychotic agent risperidone and the prolactin response in healthy subjects".
Khoury, Alexander F., et al. *JAMA*, No. 3, 394-398, 1991, "a-Blocker Therapy of Hypertension An Unfulfilled Promise".

Kirsten, R., et al., *International Journal of Clinical Pharmacology, Therapy and Toxicology*, 27 No. 7, 338-341, 1989, "Improved orthostatic dysregulation record after administration of a sustained-release form of urapidil".
Lea & Febinger, *Biopharmaceutics and Pharmacokinetics*, $3^{rd}$ Ed., Ch1., pp. 1-28, 1984. "Introduction to Pharmacokinetics".
Longer, Mark A. et al., *Remington's Pharmaceutical Sciences*, $18^{th}$ Ed, Ch 91, pp. 1676-1693, 1990. "Sustained-Release Drug Delivery Systems: Oral Dosage Forms".
Parrott, Eugene L., *Journal of Pharmaceutical Sciences*, 63(6):813-829, 1974. "Milling of Pharmaceutical Solids".
*Perry's Chemical Engineers Handbook*, Perry, Green & Maloney Editors, et al, $6^{th}$ Ed., "Introduction to Screening and Wet Classification", pp. 21.13 to 21.19, 1984.
*Physician's Desk Reference*, Thompson Healthcare, $56^{th}$ Ed., pp. 1796-1800, 2002. "Risperdal ®".
*Physician's Desk Reference*, Thompson Healthcare, $56^{th}$ Ed., pp. 1998-2001, 2002. "Concerta ®".
Ripple, Edward G., *Remington's Pharmaceutical Sciences*, $17^{th}$ Ed, Ch. 89, pp. 1585-1594, 1985. "Powders".
Roehrbom, Claus G., Adult Urology 58:6 958-959, 2001 "Efficacy and Safety of Once-Daily Alfuzosin in The Treatment of Lower Urinary Tract Symptoms and Clinical benign Prostatic Hyperplasia: a Randomized, Placebo-Controlled Trial".
Sanchez-Chapado, M. et al., European Urology,2000; 37: 421-427 "Safety and Efficacy of Sustained-Release Alfuzosin on Lower Urinary Tract Symptoms Suggestive of Benign Prostatic Hyperplasia in 3,095 Spanish Patients Evaluated during General Practice".
Santus, Giancarlo & Richard W. Baker, *Journal of Controlled Release*, 35:1-21, 1995. "Osmotic drug delivery: a review of the patent literature".
Venturella, Vincent S., *Remington's Pharmaceutical Sciences*, $17^{th}$ Ed, Ch. 25, pp. 397-427, 1985. "Natural Products".
Wurster, Dale E., *J. Am. Pharm. Assoc*, 48(8):451-454, Aug. 1959. "Air-Suspension Technique of Coating Drug Particles".
Wurster, Dale E., *J. Am. Pharm. Assoc*, 49(2):82-84, Feb. 1960. "Preparation of Compressed Tablet Granulations by the Air-Suspension Technique II".
Scott & Roff, Handbook of Common Polymers, CRC Press, Cleveland, Ohio, 1971.
Yam, Nyomi, V., U.S. Appl. No. 60/406,005.
Office Action dated Oct. 5, 2006 in U.S. Appl. No. 10/629,211.
Office Action dated Oct. 5, 2006 in U.S. Appl. No. 11/051,165.
Final Office Action dated Jun. 21, 2007 in U.S. Appl. No. 11/051,165.
Office Action dated Apr. 30, 2008 in U.S. Appl. No. 11/051,165.
Final Office Action dated Jan. 22, 2009 in U.S. Appl. No. 11/051,165.
Interview Summary dated Aug. 5, 2009 in U.S. Appl. No. 11/051,165.
Restriction Requirement dated May 16, 2008 in U.S. Appl. No. 11/051,060.
Office Action dated Jul. 8, 2009 in U.S. Appl. No. 11/051,060.
Final Office Action dated Mar. 23, 2010 in U.S. Appl. No. 11/051,060.
Office Action dated Jul. 7, 2008 in U.S. Appl. No. 11/262,113.
Interview Summary dated Feb. 20, 2009 in U.S. Appl. No. 11/262,113.
Office Action dated Sep. 28, 2009 in U.S. Appl. No. 12/349,980.
Interview Summary dated May 27, 2010 in U.S. Appl. No. 12/349,980.
Restriction Requirement dated Sep. 23, 2011 in U.S. Appl. No. 13/012,490.
Office Action dated Nov. 9, 2011 in U.S. Appl. No. 13/012,490.
Restriction Requirement dated Oct. 4, 2012 in U.S. Appl. No. 13/467,761.
Office Action dated Nov. 21, 2012 in U.S. Appl. No. 13/467,761.
Final Office Action dated Sep. 27, 2013 in U.S. Appl. No. 13/467,761.
Office Action dated Feb. 28, 2014 in U.S. Appl. No. 13/467,761.
Office Action dated May 26, 2009 in U.S. Appl. No. 11/196,556.
Notice of Opposition Jun. 18, 2008 (EP Patent No. 1539115).
Notice of Opposition_Suppl Jan. 22, 2009 (EP Patent No. 1539115).
Response to Opposition Feb. 4, 2009 (EP Patent No. 1539115).
Amended Claims Feb. 4, 2009 (EP Patent No. 1539115).

(56) References Cited

OTHER PUBLICATIONS

Annex 1 Feb. 4, 2009 (EP Patent No. 1539115).
EPO Prel Indication Oct. 29, 2009 (EP Patent No. 1539115).
EPO Notice_Letter from Opponent Jan. 28, 2010 (EP Patent No. 1539115).
Second Aux Claims Mar. 25, 2010 (EP Patent No. 1539115).
Int Decision by Opposition Division Apr. 30, 2010 (EP Patent No. 1539115).
Decision_Notice of Minutes of Oral Proceeding Apr. 30, 2010 (EP Patent No. 1539115).
Translation of Opponents Grounds of Appeal Sep. 8, 2010 (EP Patent No. 1539115).
Opponent Appeal Sep. 15, 2010 (EP Patent No. 1539115).
Response to Opponent's Appeal Jan. 25, 2011 (EP Patent No. 1539115).
Opponent Submission Sep. 21, 2011 (EP Patent No. 1539115).
Third Party Observations Apr. 27, 2012 (EP Patent No. 1539115).
Response to Third Party Observations Jul. 9, 2012 (EP Patent No. 1539115).
Minutes of Oral Proceedings Mar. 14, 2014 (EP Patent No. 1539115).
Notice of Opposition Oct. 14, 2008 (IN Patent No. 210282).
Response to Opposition Jan. 9, 2009 (IN Patent No. 210282).
Amended Claims Mar. 10, 2009 (IN Patent No. 210282).
US 6,034,101, 03/2000, Guinta et al. (withdrawn).
EPO Board of Appeal Final Decision Apr. 1, 2014 (EP Patent No. 1539115).
Invalidation trial against Korean Patent No. 10-0699516; Demandant: Whan In Pharm.; see attached trial brief as filed and English translation (KR agent ref. TIP-15-023).
Invalidation trial against Korean Patent No. 10-0699516; Demandant: Myung In Pharm; see attached trial brief as filed and English translation (KR agent ref. TIP-15-019).
Invalidation trial against Korean Patent No. 10-0699516; Demandant: Yuhan Corp.; see attached trial brief as filed and English translation (KR agent ref. TIP-15-021).
Invalidation trial against Korean Patent No. 10-0699516; Demandant: Whan In Pharm.; see attached Response to Trial Brief as filed Aug. 8, 2015 and English translation (KR agent ref. TIP-15-023).
Invalidation trial against Korean Patent No. 10-0699516; Demandant: Myung In Pharm; see attached Response to Trial Brief as filed Aug. 11, 2015 and English translation (KR agent ref. TIP-15-019).
Invalidation trial against Korean Patent No. 10-0699516; Demandant: Yuhan Corp.; see attached Response to Trial Brief as filed Aug. 11, 2015 and English translation (KR agent ref. TIP-15-021).
Invalidation trial against Korean Patent No. 10-0699516; Demandant: BC World.; see attached Trial Brief as filed Apr. 9, 2015 and English translation (KR agent ref. TIP-15-020).
Invalidation trial against Korean Patent No. 10-0699516; Demandant: BC World.; see attached Response to Trial Brief as filed Aug. 25, 2015 and English translation (KR agent ref. TIP-15-020).
Invalidation Action against Korean Patent No. 10-0699516; Petitioner: Whanin Pharm Co., LTD.; Brief filed Mar. 28, 2016.
Invalidation Action against Korean Patent No. 10-0699516; Petitioner: Whanin Pharm Co., LTD.; Brief filed Mar. 29, 2016.

* cited by examiner

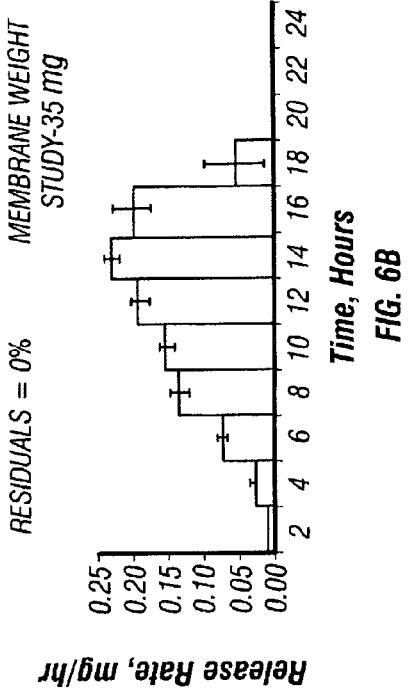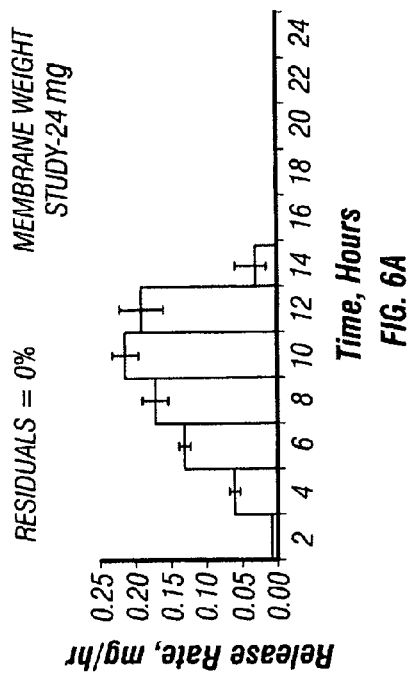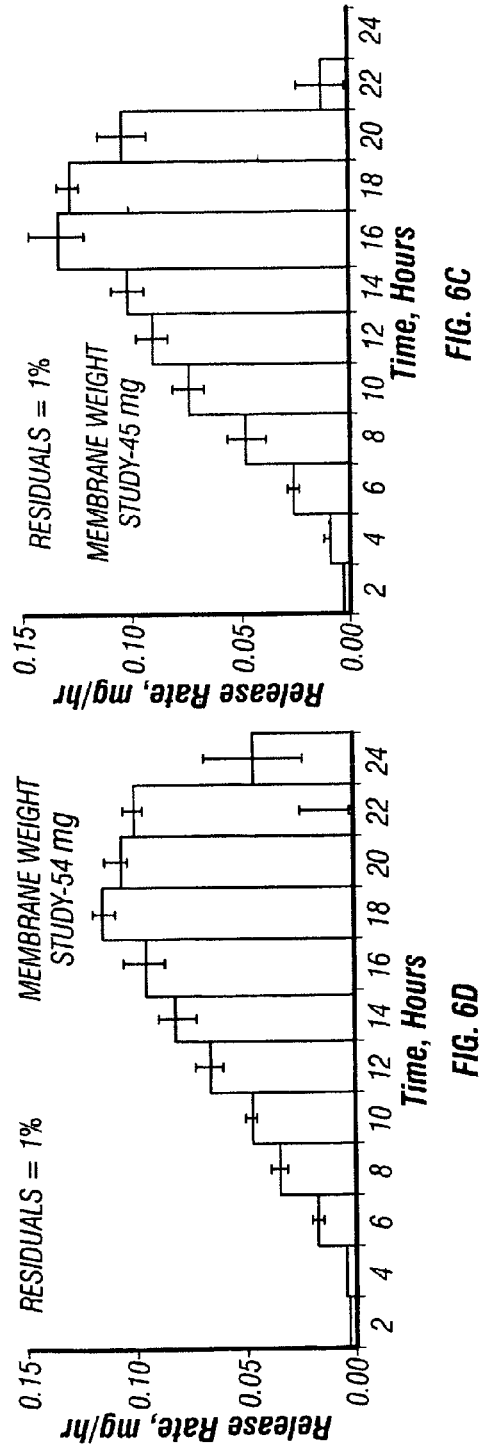
FIG. 6A
FIG. 6B
FIG. 6C
FIG. 6D

|  | STABILITY TIME POINT | ACCELERATED STABILITY CONDITIONS | |
|---|---|---|---|
|  |  | 40°C/75%RH | 50°C/75%RH |
| NON-SUBCOATED SYSTEM | T=0 | 0.66 | 0.66 |
|  | 2 WEEKS | 0.82 | 0.92 |
|  | 1 MONTH | 0.83 | 1.19 |
|  | 2 MONTHS | 1.12 | 1.65 |
|  | 3 MONTHS | 1.02 | 2.07 |
|  | 4 MONTHS | 1.10 |  |
| SUBCOATED SYSTEM | T=0 | 0.68 | 0.68 |
|  | 2 WEEKS | 0.77 | 0.79 |
|  | 1 MONTH | 0.76 | 0.98 |
|  | 2 MONTHS | 0.96 | 1.50 |
|  | 3 MONTHS | 0.88 | 1.54 |
|  | 4 MONTHS | 0.96 |  |

FIG. 8

METHODS AND DOSAGE FORMS FOR CONTROLLED DELIVERY OF PALIPERIDONE AND RISPERIDONE

CROSS REFERENCE TO RELATED APPLICATIONS

This application is a continuation of application Ser. No. 11/051,165 filed on Feb. 4, 2005 now abandoned, which is a continuation-in-part of application Ser. No. 10/629,211 filed on Jul. 28, 2003 now abandoned, and claims benefit, under 35 USC 119(e), to U.S. provisional patent application Nos. 60/399,590, filed Jul. 29, 2002, and 60/406,005 filed Aug. 26, 2002, all of which are incorporated herein by reference.

FIELD OF THE INVENTION

This invention pertains to the controlled delivery of pharmaceutical agents and methods, dosage forms and devices. In particular, the invention is directed to methods, dosage forms and devices for the controlled delivery of paliperidone or risperidone, with reduced degradation of the active agent.

BACKGROUND OF THE INVENTION

The art is replete with descriptions of oral dosage forms for the controlled release of pharmaceutical agents. While a variety of sustained release dosage forms for delivering certain drugs exhibiting short half-life may be known, not every drug may be suitably delivered from those dosage forms because of solubility, metabolic processes, absorption and other physical, chemical and physiological parameters that may be unique to the drug and the mode of delivery. Examples of such drugs that are not likely candidates for controlled release dosage forms are those exhibiting a long half-life such as paliperidone. It has also been found that paliperidone degrades into notable amounts of impurities. The major degradation products include C-9 ketone, N-oxides, and various dimmers of its degradants.

Paliperidone is more fully described in U.S. Pat. No. 4,804,663. The paliperidone compound differs from risperidone and related prior art compounds described in U.S. Pat. Nos. 4,352,811 and 4,458,076 by its substitution on the 1-position of the piperidine moiety.

Paliperidone and risperidone are practically insoluble in water. Additionally, since paliperidone has a long half-life of about one day, it is not a typical candidate for extended delivery. However, side effects such as anxiety, somnolence, dizziness, constipation, extrapyramidal symptoms, and orthostatic hypotension may be related to high blood plasma concentration levels restricting the ability to administer a single daily immediate release dose.

It is expected that the side effects are likely a result of either rate of rise and/or actual drug blood plasma concentrations exceeding a threshold maximum tolerable concentration (MTC). However, in order to obtain a therapeutic effect, concentrations need to be sustained above a minimum pharmacodynamic concentration (MPC).

Another aspect of delivery of paliperidone is that administration may require low drug loading in the dosage form. Dosage forms may need to contain drug in the range of 0.5% to 20% or 5% to 20% of the overall weight of the dosage form. In one embodiment of the present invention the solid dosage form will contain from about 0.5 mg to about 25 mg, preferably from 1 to about 20 mg, more preferably from about 3 to about 18 mg of paliperidone or risperidone salts or esters thereof. The low drug loading requirement presents problems in formulating compositions and fabricating dosage forms that are suitable for oral administration that deliver at the desired rate of release for an extended period of time.

Prior art osmotic dosage forms mention delivery of risperidone from a liquid gelatin capsule without mention of delivery of paliperidone or of a preferred rate of delivery or identification of a solid capsule dosage form. Published patent application by ALZA Corporation, WO 00/35419.

Other art discloses delivery of risperidone through transdermal methods with patches without claiming any rate of release or desired plasma concentration profile. Published patent application by Janssen, WO 96/31201. Furthermore, this art does not identify delivery of paliperidone much less delivery of paliperidone through oral controlled release delivery.

There is also art disclosing delivery of risperidone and/or paliperidone through injectable implants for long term, multi-day, delivery. This art includes the published patent application by Alkermes WO 01/34120, and U.S. Pat. Nos. 5,654,008; 5,650,173; 5,770,231; 6,077,843; 6,368,632; 6,110,923; 5,965,168; and 5,692,477 by Alkermes. US patents claiming injectable dosage forms to provide almost zero order delivery include U.S. Pat. Nos. 5,871,778 and 5,656,299 by Yoishitomi Pharmaceutical Industries. This art does not disclose preferred release rates and does not teach or motivate toward an ascending rate of release, much less such release through an oral delivery system.

Prior art for oral delivery does not address delivery of extended, controlled release paliperidone.

Oral controlled release dosage forms include, U.S. Pat. No. 5,536,507 which describes a three component pharmaceutical formulation that utilizes, inter alia, a pH sensitive polymer and optionally an osmotic agent that will swell in the higher pH regions of the lower portion of the small intestine and the large intestine to release drug in those environments. Additional components of the dosage form include a delayed release coating and an enteric coating to provide a dosage form that releases very little, if any, of the drug in the stomach, a relatively minimal amount in the small intestine and reportedly about 85% or more in the large intestine. Such a dosage form provides for a widely varying time-release of drug after administration that may not begin for 1-3 hours until the dosage form has passed from the stomach and an additional 3 hours or more for the dosage form to pass into the large intestine.

Exemplary sustained release paliperidone or risperidone (salts or esters) dosage forms, methods of preparing such dosage forms and methods of using such dosage forms described herein are directed to osmotic dosage forms for oral administration.

In addition to osmotic systems as described herein, however, there are many other approaches to achieving sustained release of drugs from oral dosage forms known in the art. These different approaches include, for example, diffusion systems such as reservoir devices and matrix devices, dissolution systems such as encapsulated dissolution systems (including, for example, "tiny time pills") and matrix dissolution systems, combination diffusion/dissolution systems and ion-exchange resin systems as described in *Remington's Pharmaceutical Sciences*, 1990 ed., pp. 1682-1685. Paliperidone or risperidone dosage forms that operate in accord with these other approaches are encompassed by the scope of the disclosure herein to the extent that the drug release characteristics and/or the blood plasma paliperidone concentration characteristics as recited herein and in the claims describe those dosage forms either literally or equivalently.

Osmotic dosage forms in general utilize osmotic pressure to generate a driving force for imbibing fluid into a compartment formed, at least in part, by a semipermeable membrane that permits free diffusion of fluid but not drug or osmotic agent(s), if present. A significant advantage to osmotic systems is that operation is pH-independent and thus continues at the osmotically determined rate throughout an extended time period even as the dosage form transits the gastrointestinal tract and encounters differing microenvironments having significantly different pH values. A review of such dosage forms is found in Santus and Baker, "Osmotic drug delivery: a review of the patent literature," *Journal of Controlled Release* 35 (1995) 1-21, incorporated in its entirety by reference herein. In particular, the following U.S. patents, owned by the assignee of the present application, ALZA Corporation, directed to osmotic dosage forms, are each incorporated in their entirety herein: U.S. Pat. Nos. 3,845,770; 3,916,899; 3,995,631; 4,008,719; 4,111,202; 4,160,020; 4,327,725; 4,519,801; 4,578,075; 4,681,583; 5,019,397; and 5,156,850.

Devices in which a drug composition is delivered as a slurry, suspension or solution from a small exit orifice by the action of an expandable layer are described in U.S. Pat. Nos. 5,633,011; 5,190,765; 5,252,338; 5,620,705; 4,931,285; 5,006,346; 5,024,842; and 5,160,743, which are incorporated herein by reference. Typical devices include an expandable push layer and a drug layer surrounded by a semipermeable membrane. In certain instances, the drug layer is provided with a subcoat to delay release of the drug composition to the environment of use or to form an annealed coating in conjunction with the semipermeable membrane.

Devices in which a drug composition is delivered in a dry state from a large exit orifice by the action of an expandable layer are described in U.S. Pat. Nos. 4,892,778, 4,915,949 and 4,940,465. Those references describe a dispenser for delivering a beneficial agent to an environment of use that includes a semipermeable wall containing a layer of expandable material that pushes a dry drug layer out of the compartment formed by the wall. The exit orifice in the device is substantially the same diameter as the inner diameter of the compartment formed by the wall.

While dosage forms delivering the drug composition to the environment of use in the dry state may provide suitable release of drug at various drug loadings over a prolonged period of time, the exposure of the drug layer to the environment of use may result in agitation-dependent release of drug that in some circumstances is difficult to control. Accordingly, it may be advantageous to release the drug as a slurry or suspension that may be metered by control of rate of expansion of the push layer and the size of the exit orifice in the dosage form as in accordance with this invention.

U.S. Pat. No. 5,169,638 describes a buoyant controlled release pharmaceutical powder formulation to be filled into capsules that uses a pH dependent polymer formed from alginic acid and hydroxypropylmethyl cellulose to release pharmaceuticals at a controlled rate. It appears that this capsule formulation was intended to mimic the characteristics of a tableted formulation.

No description is provided of a formulation that provides the uniform release characteristics of the dosage forms containing paliperidone and related compounds of the present invention.

U.S. Pat. Nos. 4,892,778 and 4,940,465, describe a dispenser for delivering a beneficial agent to an environment of use that includes a semipermeable wall containing a layer of expandable material that pushes a drug layer out of the compartment formed by the wall. The exit orifice in the device is substantially the same diameter as the inner diameter of the compartment formed by the wall.

U.S. Pat. No. 4,915,949, describes a dispenser for delivering a beneficial agent to an environment of use that includes a semipermeable wall containing a layer of expandable material that pushes a drug layer out of the compartment formed by the wall. The drug layer contains discrete tiny pills dispersed in a carrier. The exit orifice in the device is substantially the same diameter as the inner diameter of the compartment formed by the wall.

U.S. Pat. No. 5,126,142, describes a device for delivering an ionophore to livestock that includes a semipermeable housing in which a composition containing the ionophore and a carrier and an expandable hydrophilic layer is located, along with an additional element that imparts sufficient density to the device to retain it in the rumen-reticular sac of a ruminant animal. The ionophore and carrier are present in a dry state during storage and the composition changes to a dispensable, fluid-like state when it is in contact with the fluid environment of use. A number of different exit arrangements are described, including a plurality of holes in the end of the device and a single exit of varying diameter to control the amount of drug released per unit time due to diffusion and osmotic pumping.

Prior to this invention, paliperidone's related compound, risperidone, was administered in conventional forms, such as a nonrate-controlling, dose-dumping immediate release tablet, or by a dose-dumping capsule, and usually at multiple, repetitive dosing intervals throughout the day. The product is marketed as Risperdal® by Janssen Pharmaceutica Products, L. P. *Physicians' Desk Reference*, Thompson Healthcare, 56$^{th}$ Ed., pp. 1796-1800 (2002).

The Risperdal® mode of therapy, however, continues to lead to an initial high dose of risperidone in the blood plasma after administration, followed by a decreased level of risperidone in the blood plasma. Moreover, this peak and trough occurs twice to three times during a 24-hour period due to the multiple dosing regimen. The concentration differences in dosing patterns are related to the presence and absence of administered drug, which is a major disadvantage, associated with this prior dosage form and mode of administration.

Conventional dosage forms and their mode of operation, including dose peaks and valleys, are discussed in *Pharmaceutical Sciences*, Remington, 18th Ed., pp. 1676-1686 (1990), Mack Publishing Co.; *The Pharmaceutical and Clinical Pharmacokinetics*, 3rd Ed., pp. 1-28 (1984), Lea and Febreger, Philadelphia; and in U.S. Pat. Nos. 3,598,122 and 3,598,123, both issued to Zaffaroni.

A dosage form exhibiting substantially ascending release rate profile is Concerta® marketed by McNeil Consumer Healthcare and ALZA Pharmaceuticals. *Physicians' Desk Reference*, Thompson Healthcare, 56$^{th}$ Ed., pp. 1998-2001 (2002). The Concerta® product, however indicated for once-a-day administration, only delivers at a substantially ascending rate of release for up to about 8 hours.

Patent applications relating to Concerta® include published PCT Pat. Application No. WO99/62496A1. This patent application discloses the substantially ascending release rate profile related to Concerta® for delivery over about 8 hours for once-a-day dosing.

Related patent applications include published PCT Pat. Application No. WO98/14168; WO98/23263; WO 98/06380A2 and US 2001/0012847A1.

Still other applications relating to providing increasing rate of release delivery profile include US 2002/0035357A1; WO 01/52819A1 and WO 01/37813A2 & A3.

There remains a need for effective dosing methods, dosage forms and devices that will permit the controlled release of paliperidone and related compounds over a prolonged period of time at a substantially ascending rate of release to reduce the amount of the active agent that the patient is initially exposed to and to increase the time between dosing, preferably to obtain a once-a-day dosing regimen while reducing associated side effects.

SUMMARY OF THE INVENTION

The present invention is designed for once-a-day administration of an oral dosage form to deliver paliperidone or risperidone for more than about 22 hours utilizing a capsule-shaped tablet. This approximately 22 hours of release is at a substantially ascending rate of release from the core with 90% delivery occurring at about 20 hours. This novel profile provides therapeutic delivery above the MPC while keeping the plasma levels below the MTC and low enough such that side effects will be reduced and the development of tolerance is increased to the side effects that are associated with paliperidone and risperidone. This delivery profile provides 24 hours of efficacy without initially undesirable high plasma levels.

The present invention provides for a substantially ascending release rate. It has been surprisingly discovered that the instant ascending release profile (that provides a maximum blood plasma concentration that occurs at more than about 6 hours following the initial dose, preferably more than 8 hours following the initial dose such as between 14 and 22 hours after the dose) best provides efficacious therapy over 24 hours while potentially reducing negative side effects associated with administration of the drug.

The present invention utilizes a slow, but substantially ascending, rate of release when the dosage form is likely to be in the colonic region of the gastrointestinal (GI) tract. The profile is not previously used to deliver any drug, but is designed to increase the therapeutic index of paliperidone and risperidone.

It has been surprisingly found that the described ascending release rate can provide for a substantially ascending blood plasma concentration of drug with peak concentration occurring later than about 16 hours after administration. This ascending blood plasma concentration increases the intraday tolerance to side effects.

It has been further surprisingly discovered that the addition of an osmagent, salt, into the first drug layer, but not in the second drug layer, impacts the delivery profile such that a substantially ascending release rate results.

It has been further surprisingly discovered that maintaining the ratio of the concentration of drug in the first drug layer and the concentration of drug in the second drug layer impacts the delivery profile such that the desired substantially ascending rate of release results.

The dosage form utilizes a semipermeable membrane surrounding a three-layer core: the first layer is referred to as a first drug layer and contains low amounts of drug and an osmotic agent such as salt; the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet.

In the aqueous environment of the GI tract, water is imbibed through the semipermeable membrane at a controlled rate determined by the properties of the membrane and the osmolality of the core constituents. This causes the push layer to swell and the drug layers to hydrate and form viscous, but deformable, masses. The push layer expands against the second drug layer, which in turn pushes against the hydrated first drug layer. The first drug layer, followed by the second drug layer, exits the system through the orifice(s) in the membrane at the same rate that water is imbibed into the core. The biologically inert components of the tablet remain intact during the GI transit and are eliminated as a shell along with insoluble core components.

The dosage form incorporating the present invention is designed to be a once-a-day dosage form that is therapeutically effective while providing increased stability.

In still another aspect, the invention describes a dosage form comprising a membrane defining a compartment, the membrane surrounding an inner protective subcoat, at least one exit orifice formed or formable therein and at least a portion of the membrane being semipermeable; an expandable layer located within the compartment remote from the exit orifice and in fluid communication with the semipermeable portion of the membrane; a first drug layer located adjacent the exit orifice; and a second drug layer located within the compartment between the first drug layer and the expandable layer, the drug layers comprising the compound paliperidone or risperidone or a pharmaceutically acceptable acid addition salt thereof.

As the drug is relatively insoluble, the first drug layer has a tendency not to mix into the second drug layer. Depending upon the relative viscosity of the first drug layer and second drug layer, different release profiles are obtained. It is imperative to identify the optimum viscosity for each layer. In the present invention, viscosity is modulated by addition of salt, sodium chloride.

The delivery profile from the core is dependent on the weight, formulation and thickness of each of the drug layers.

The ratio of core diameter to core length is also an important factor. The shape of the system as a capsule shaped tablet is an important feature contributing to the substantially ascending profile from the core.

The delivery system is designed to achieve maximum blood plasma concentrations more than about 6 hours following the initial dose, or more than 8 hours following the initial dose, or more than about 12 hours after the initial dose, or more than 14 hours after the initial dose preferably between 14 and 22 hours, more preferably between about 16 and about 22 hours and preferably between 18 and 21 hours after dosing. Peak concentrations most preferably occur between approximately hour 18 and hour 20.

The present invention is designed to be a once-a-day dosage form that is therapeutically effective while producing fewer side effects than an immediate release dosage form administered multiple times per day. The present invention provides two key features: a substantially ascending delivery that affects the pharmacodynamics and development of tolerance to the side effect, and the substantially ascending delivery provides adequate plasma concentrations for pharmacological effect.

In one aspect, the invention comprises a sustained release dosage form adapted to release over a prolonged period of time at a substantially ascending rate of release, the compound paliperidone or risperidone.

In another aspect, the invention comprises a method of treating a condition in a subject responsive to administration of paliperidone or risperidone or a pharmaceutically acceptable acid addition salt thereof, which comprises orally administering to the subject a dosage form adapted to release the compound at a substantially ascending rate of release over a prolonged period of time. Most preferably, the dosage form is administered orally, once a day.

In still another aspect, the invention comprises a dosage form comprising a membrane defining a compartment, the membrane having at least one exit orifice formed or formable therein and at least a portion of the membrane being semipermeable; an expandable layer located within the compartment remote from the exit orifice and in fluid communication with the semipermeable portion of the membrane; a first drug layer located adjacent the exit orifice; and a second drug layer located within the compartment between the first drug layer and the expandable layer, the drug layers comprising the compound paliperidone or risperidone or a pharmaceutically acceptable salt thereof.

In still another aspect, the invention comprises a dosage form comprising a membrane defining a compartment, the membrane having at least one exit orifice formed or formable therein and at least a portion of the membrane being semipermeable; an expandable layer located within the compartment remote from the exit orifice and in fluid communication with the semipermeable portion of the membrane; a first drug layer located adjacent the exit orifice; and a second drug layer located within the compartment between the first drug layer and the expandable layer, the drug layers comprising the compound paliperidone or risperidone or a pharmaceutically acceptable salt thereof, and the first drug layer comprising salt and the second drug layer containing no salt.

In still another aspect, the invention comprises a dosage form comprising a membrane defining a compartment, the membrane having at least one exit orifice formed or formable therein and at least a portion of the membrane being semipermeable; an expandable layer located within the compartment remote from the exit orifice and in fluid communication with the semipermeable portion of the membrane; a first drug layer located adjacent the exit orifice; and a second drug layer located within the compartment between the first drug layer and the expandable layer, the drug layers comprising the compound paliperidone or risperidone or a pharmaceutically acceptable salt thereof second drug layer.

The dosage form may optionally comprise a flow-promoting layer between the membrane and the drug layers.

In another aspect, the invention comprises a method of treating a condition responsive to administration of paliperidone or risperidone or a pharmaceutically acceptable acid addition salt thereof, which comprises administering the compound to provide a substantially ascending plasma concentration of the compound. The $C_{max}$ occurs at a time greater than about 14 hours, greater than about 16 hours, greater than about 18 hours and preferably at about 20 hours.

BRIEF DESCRIPTION OF THE FIGURES

FIGS. 6A, 6B, 6C and 6D illustrate the effect of membrane weight on rate of release of paliperidone;

FIG. 8 illustrates tabular comparison of dosage form stability with and without use of the protective subcoat of the present invention;

DETAILED DESCRIPTION OF THE INVENTION

Figure 1:
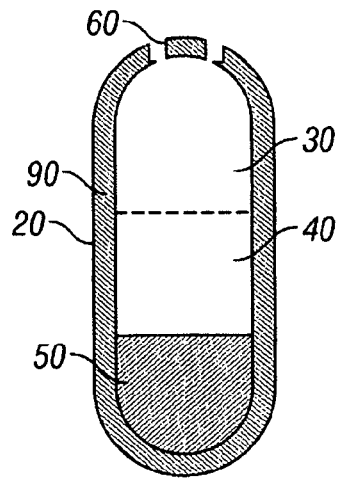
FIG. 1 illustrates a two-orifice embodiment of the present invention, prior to administration to a subject.
Figure 2:
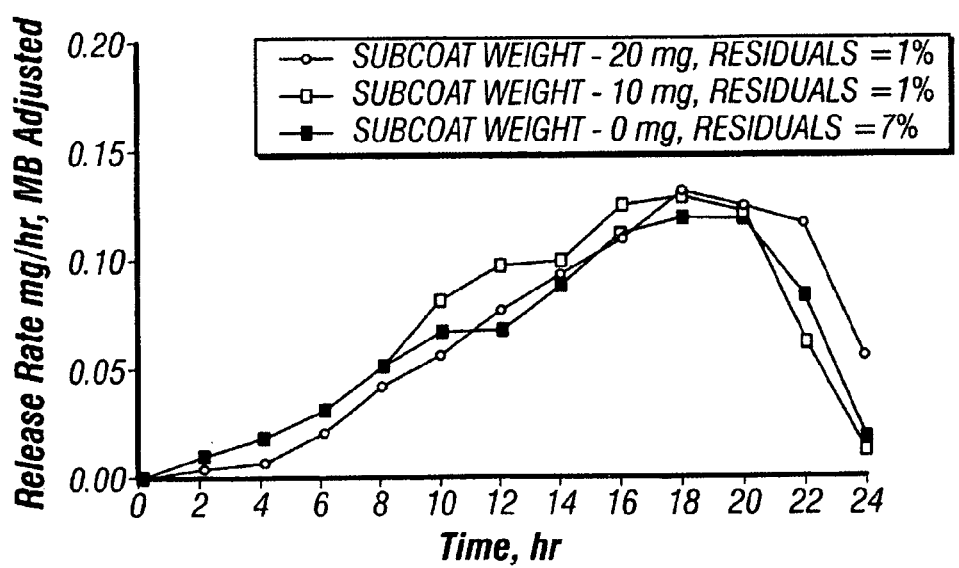
FIG. 2 illustrates the model delivery profile providing a substantially ascending rate of release of paliperidone demonstrating the effect of different weights of subcoats.

The present invention is best understood by reference to the following definitions, the drawings and exemplary disclosure provided herein.

Definitions

By "dosage form" is meant a pharmaceutical composition or device comprising a pharmaceutically active agent, such as paliperidone or risperidone or a pharmaceutically acceptable salt thereof, the composition or device optionally containing inactive ingredients, i.e., pharmaceutically acceptable excipients such as suspending agents, surfactants, disintegrants, binders, diluents, lubricants, stabilizers, antioxidants, osmotic agents, colorants, plasticizers, coatings and the like, that are used to manufacture and deliver active pharmaceutical agents.

By "active agent", "drug", or "compound" is meant an agent, drug, or compound having the characteristics of paliperidone or risperidone or a pharmaceutically acceptable acid addition salt thereof.

By "pharmaceutically-acceptable acid addition salt" or "pharmaceutically acceptable salt", which are used interchangeably herein, are meant those salts in which the anion does not contribute significantly to the toxicity or pharmacological activity of the salt, and, as such, they are the pharmacological equivalents of the bases of the paliperidone or risperidone compound. Examples of pharmaceutically acceptable acids that are useful for the purposes of salt formation include but are not limited to hydrochloric, hydrobromic, hydroiodic, citric, acetic, benzoic, mandelic, phosphoric, nitric, mucic, isethionic, palmitic, and others.

The expressions "exit," "exit orifice," "delivery orifice" or "drug delivery orifice," and other similar expressions, as may be used herein include a member selected from the group consisting of a passageway; an aperture; an orifice; and a bore. The expression also includes an orifice that is formed or formable from a substance or polymer that erodes, dissolves or is leached from the outer wall to thereby form an exit orifice. The expression includes one or multiple passageways, apertures, orifices, bores or pores.

A drug "release rate" refers to the quantity of drug released from a dosage form per unit time, e.g., milligrams of drug released per hour (mg/hr). Drug release rates for drug dosage forms are typically measured as an in vitro rate of dissolution, i.e., a quantity of drug released from the dosage form per unit time measured under appropriate conditions and in a suitable fluid. The dissolution tests described herein were performed on dosage forms placed in metal coil sample holders attached to a USP Type VII bath indexer in a constant temperature water bath at 37° C. Aliquots of the release rate solutions were injected into a chromatographic system to quantify the amounts of drug released during the testing intervals.

By "release rate assay" is meant a standardized assay for the determination of the release rate of a compound from the dosage form tested using a USP Type VII interval release apparatus. It is understood that reagents of equivalent grade may be substituted in the assay in accordance with generally accepted procedures.

For clarity and convenience herein, the convention is utilized of designating the time of drug administration as zero hours (t=0 hours) and times following administration in appropriate time units, e.g., t=30 minutes or t=2 hours, etc.

As used herein, unless otherwise specified, a drug release rate obtained at a specified time "following administration" refers to the in vitro drug release rate obtained at the specified time following implementation of an appropriate dissolution test. The time at which a specified percentage of the drug within a dosage form has been released may be referenced as the "$T_x$" value, where "x" is the percent of drug that has been released. For example, a commonly used reference measurement for evaluating drug release from dosage forms is the time at which 70% or 90% of drug within the dosage form has been released. This measurement is referred to as the "$T_{70}$" or "$T_{90}$" for the dosage form.

By "immediate-release dosage form" is meant a dosage form that releases drug substantially completely within a short time period following administration, i.e., generally within a few minutes to about 1 hour.

By "extended release dosage form" or "controlled release dosage form" is meant a dosage form that releases drug in a substantially consistent predetermined rate for many hours. Controlled release dosage forms in accord with the present invention exhibit $T_{90}$ values of at least about 8 hours, at least about 14 hours, at least about 16 hours, at least about 18 hours or more and preferably about 20 hours or more. The dosage forms release drug over periods of time of at least about 8 hours, at least about 14 hours, at least about 16 hours, preferably 18 hours or more and, more preferably, 20 hours or more.

By "sustained release dosage form" is meant a dosage form that releases drug substantially continuously for many hours. Sustained release dosage forms of the present invention release drug over periods of time of at least about 8 hours, at least 14 hours, at least 16 hours, at least 18 hours, preferably about 20 hours or more and, more preferably, about 20 hours or more.

Dosage forms in accord with the present invention exhibit controlled release rates of paliperidone or risperidone for a prolonged period of time.

By "sustained release" is meant a predetermined continuous release of active agent to an environment over a prolonged period of time.

By "uniform release rate" is meant an average hourly release rate from the core that varies positively or negatively by no more than about 30% and preferably no more than about 25%, most preferably no more than about 10%, from either the preceding or the subsequent average hourly release rate as determined in a USP Type VII Interval Release Apparatus where the cumulative release is between 25% and 75%.

By "prolonged period of time" is meant a continuous period of time of at least about 8 hours, preferably 10-14 hours or more and, more preferably, 16 hours or more. For example, the exemplary osmotic dosage forms described herein generally begin releasing paliperidone at about one hour following administration and the uniform rate of release, as defined above, continues for a prolonged period of time from about 25% to until at least about 75% and preferably at least about 85% of the drug is released from the dosage form. Release of paliperidone continues thereafter for several more hours although the rate of release is generally slowed somewhat from the uniform release rate.

By "C" is meant the concentration of drug in the blood plasma of a subject, generally expressed as mass per unit volume, typically nanograms per milliliter. For convenience, this concentration may be referred to as "plasma drug concentration" or "plasma concentration" herein which is intended to be inclusive of drug concentration measured in any appropriate body fluid or tissue. The plasma drug concentration at any time following drug administration is referenced as $C_{time}$, as in $C_{9h}$ or $C_{24h}$, etc.

By "steady state" is meant the condition in which the amount of drug present in the blood plasma of a subject does not vary significantly over a prolonged period of time. A pattern of drug accumulation following continuous administration of a constant dose and dosage form at constant dosing intervals eventually achieves a "steady-state" where the plasma concentration peaks and plasma concentration troughs are essentially identical within each dosing interval. As used herein, the steady-state maximal (peak) plasma drug concentration is referenced as $C_{max}$ and the minimal (trough) plasma drug concentration is referenced as $C_{min}$. The times following drug administration at which the steady-state peak plasma and trough drug concentrations occur are referenced as the $T_{max}$ and the $T_{min}$, respectively.

"Ascending rate of release" or "ascending release rate" means a rate of release wherein the amount of drug released from a dosage form as a function of time increases over a period of time, preferably continuously and gradually. Preferably, the rate of drug released as a function of time increases in a steady (rather than step-wise) manner. More preferably, an ascending rate of release may be characterized as follows. The rate of release as a function of time for a dosage form is measured and plotted as % drug release versus time or as milligrams of drug released/hour versus time. An ascending rate of release is characterized by an average rate (expressed in mg of drug per hour) wherein the rate within a given two hour span is higher as compared with the previous two hour time span, over the period of time of about 2 hours to about 12 hours, preferably, about 2 hours to about 18 hours, more preferably about 4 hours to about 12 hours, more preferably still, about 4 hours to about 18 hours. Preferably, the increase in average rate is gradual such that less than about 30% of the dose is delivered during any 2 hour interval, more preferably, less than about 25% of the dose is delivered during any 2 hour interval. Preferably, the ascending release rate is maintained until at least about 50%, more preferably until at least about 75% of the drug in the dosage form has been released.

One skilled in the art will recognize that as the increase in the area under the curve increases (e.g from 1% to 10%), the total time over which the drug is released from the dosage form will necessarily decrease and as such the determination of ascending rate of release will span a shorter overall period of time.

Persons of skill in the art appreciate that plasma drug concentrations obtained in individual subjects will vary due to intrapatient variability in the many parameters affecting drug absorption, distribution, metabolism and excretion. For this reason, unless otherwise indicated, mean values obtained from groups of subjects are used herein for purposes of comparing plasma drug concentration data and for analyzing relationships between in vitro dosage form dissolution rates and in vivo plasma drug concentrations.

A relationship between an administered dose of paliperidone and the magnitude of the peak plasma paliperidone concentration obtained following dose administration is used herein to illustrate significant differences between the dosage forms and methods of the present invention and prior art dosage forms. For example, as described below in more detail, a numerical value is derived by calculating the ratio of the numerical value of the mean $C_{max}$(ng/ml) to the numerical value of the dose (mg), i.e., $C_{max}$/dose. The difference in the values of the derived ratios characterize the reduction in the magnitude of peak plasma paliperidone concentrations following administration of the sustained release paliperidone dosage forms of the present invention compared to peak plasma paliperidone concentrations following administration of conventional immediate-release paliperidone dosage forms. Administration of dosage forms in accord with the present invention preferably provides steady-state $C_{max}$/dose ratios of less than about 30 and more preferably less than about 25.

It has been surprisingly discovered that sustained release paliperidone dosage forms exhibiting $T_{90}$ values of about 8 hours or more, 14 hours or more, 16 hours or more, 18 hours or more and more preferably about 20 hours or more and which release paliperidone at a controlled release rate for a prolonged period of time can be prepared. Administration of such dosage forms once daily provides therapeutically effective average steady-state plasma paliperidone concentrations.

The exemplary sustained release paliperidone dosage forms, methods of preparing such dosage forms and methods of using such dosage forms described herein are directed to osmotic dosage forms for oral administration. In addition to osmotic systems as described herein, however, there are many other approaches to achieving sustained release of drugs from oral dosage forms known in the art. These different approaches may include, for example, diffusion systems such as reservoir devices and matrix devices, dissolution systems such as encapsulated dissolution systems (including, for example, "tiny time pills") and matrix dissolution systems, combination diffusion/dissolution systems and ion-exchange resin systems as described in *Remington's Pharmaceutical Sciences*, 1990 ed., pp. 1682-1685. Paliperidone dosage forms that operate in accord with these other approaches are encompassed by the scope of the claims below to the extent that the drug release characteristics and/or the plasma paliperidone concentration characteristics as recited in the claims describe those dosage forms either literally or equivalently.

Osmotic dosage forms, in general, utilize osmotic pressure to generate a driving force for imbibing fluid into a compartment formed, at least in part, by a semipermeable wall that permits free diffusion of fluid but not drug or osmotic agent(s), if present. A significant advantage to osmotic systems is that operation is pH-independent and thus continues at the osmotically determined rate throughout an extended time period even as the dosage form transits the gastrointestinal tract and encounters differing microenvironments having significantly different pH values. A review of such dosage forms is found in Santus and Baker, "Osmotic drug delivery: a review of the patent literature," *Journal of Controlled Release* 35 (1995) 1-21. In particular, the following U.S. patents, owned by the assignee of the present application, ALZA Corporation, directed to osmotic dosage forms, are each incorporated in their entirety herein: U.S. Pat. Nos. 3,845,770; 3,916,899; 3,995,631; 4,008,719; 4,111,202; 4,160,020; 4,327,725; 4,519,801; 4,578,075; 4,681,583; 5,019,397; and 5,156,850.

FIG. 1 is a cutaway view of one embodiment of dosage form 10 in accord with the present invention. In this embodiment, the internal compartment defined by membrane 20 contains a multilayer-compressed core having a first component drug layer 30, a second component drug layer 40 and a third component push layer 50.

While the preferred embodiment in FIG. 1 illustrates a capsule-shaped tablet, the tablet geometry may be other shapes including a standard biconvex shape. Such a preferred shape as well as other alternate shapes will impact and alter release rates.

In operation, following oral ingestion of dosage form 10, the osmotic activity gradient across wall 20 causes gastric fluid to be imbibed through wall 20 thereby converting first drug layer 30 and second drug layer 40 into deliverable compositions, i.e. solutions or suspensions, and concurrently swelling the osmopolymer(s) in push layer 50. The deliverable first drug layer 30 and second drug layer 40 are released through exits 60 as fluid continues to enter the internal compartment and push layer 50 continues to swell. As release of first drug layer 30 and second drug layer 40 occurs, fluid continues to be imbibed and push layer 50 continues to swell thereby driving continued release. In this manner, drug is released in a continuous manner over an extended time period.

As described in more detail below, third component push layer 50 comprises osmotically active component(s), but does not contain active drug. The osmotically active component(s) in push layer 50 typically comprises an osmagent and one or more osmopolymer(s) having relatively large molecular weights which exhibit swelling as fluid is imbibed such that significant release of these osmopolymers through exits 60 does not occur. Additional excipients such as binders, lubricants, antioxidants and colorants may also be included in push layer 50. The third component layer is referred to herein as an expandable or a push layer since, as fluid is imbibed, the osmopolymer(s) swell and push against the deliverable drug formulation of the second component drug layer to thereby facilitate release of the drug formulation from the dosage form.

As described in more detail below, first component drug layer 30 comprises osmotically active components, and a lower amount of active drug than in second component drug layer 40. The osmotically active component(s) in the first component drug layer comprises an osmagent such as salt and one or more osmopolymer(s) having relatively small molecular weights which exhibit swelling as fluid is imbibed such that release of these osmopolymers through exit 60 occurs similar to that of drug layer 40. Additional excipients such as binders, lubricants, antioxidants and colorants may also be included in first drug layer 30.

Second drug layer 40 comprises paliperidone in an admixture with selected excipients adapted to provide an osmotic activity gradient for driving fluid from an external environment through membrane 20 and for forming a deliverable drug formulation upon imbibition of fluid. The excipients may include a suitable suspending agent, also referred to herein as a drug carrier, but no osmotically active agent, "osmagent," such as salt, sodium chloride. It has been surprisingly discovered that the omission of salt from this second drug layer, which contains a higher proportion of the overall drug in the dosage form, in combination with the salt in the first drug layer component, provides an improved ascending rate of release creating a longer duration of ascending rate.

Drug layer 40 has a higher concentration of the drug than does drug layer 30. The ratio of the concentration of drug in the first drug layer 30 to the concentration of drug in the second drug layer 40 is maintained at less than 1 and preferably less than 0.33 to provide the desired substantially ascending rate of release.

Drug layer 40 may also comprise other excipients such as lubricants, binders, etc.

Drug layer 40, as with drug layer 30, further comprises a hydrophilic polymer carrier. The hydrophilic polymer provides a particle in the drug composition that contributes to the controlled delivery of the active drug. Representative examples of these polymers are poly(alkylene oxide) of 100,000 to 750,000 number-average molecular weight, including poly(ethylene oxide), poly(methylene oxide), poly(butylene oxide) and poly(hexylene oxide); and a poly(carboxymethylcellulose) of 40,000 to 400,000 number-average molecular weight, represented by poly(alkali carboxymethylcellulose), poly(sodium carboxymethylcellulose), poly(potassium carboxymethylcellulose) and poly(lithium carboxymethylcellulose). Drug layer 40 can further comprise a hydroxypropylalkylcellulose of 9,200 to 125,000 number-average molecular weight for enhancing the delivery properties of the dosage form as represented by hydroxypropylethylcellulose, hydroxypropylmethylcellulose, hydroxypropylbutylcellulose and hydroxypropylpentylcellulose; and a poly(vinylpyrrolidone) of 7,000 to 75,000 number-average molecular weight for enhancing the flow properties of the dosage form. Preferred among these polymers are the poly(ethylene oxide) of 100,000-300,000 number average molecular weight. Carriers that erode in the gastric environment, i.e., bioerodible carriers, are especially preferred.

Other carriers that may be incorporated into drug layer 40, and/or drug layer 30, include carbohydrates that exhibit sufficient osmotic activity to be used alone or with other osmagents. Such carbohydrates comprise monosaccharides, disaccharides and polysaccharides. Representative examples include maltodextrins (i.e., glucose polymers produced by the hydrolysis of corn starch) and the sugars comprising lactose, glucose, raffinose, sucrose, mannitol, sorbitol, and the like. Preferred maltodextrins are those having a dextrose equivalence (DE) of 20 or less, preferably with a DE ranging from about 4 to about 20, and often 9-20. Maltodextrin having a DE of 9-12 has been found to be useful.

Drug layer 40 and drug layer 30 typically will be a substantially dry, <1% water by weight, composition formed by compression of the carrier, the drug, and other excipients as one layer.

Drug layer 40 may be formed from particles by comminution that produces the size of the drug and the size of the accompanying polymer used in the fabrication of the drug layer, typically as a core containing the compound, according to the mode and the manner of the invention. The means for producing particles include granulation, spray drying, sieving, lyophilization, crushing, grinding, jet milling, micronizing and chopping to produce the intended micron particle size. The process can be performed by size reduction equipment, such as a micropulverizer mill, a fluid energy grinding mill, a grinding mill, a roller mill, a hammer mill, an attrition mill, a chaser mill, a ball mill, a vibrating ball mill, an impact pulverizer mill, a centrifugal pulverizer, a coarse crusher and a fine crusher. The size of the particle can be ascertained by screening, including a grizzly screen, a flat screen, a vibrating screen, a revolving screen, a shaking screen, an oscillating screen and a reciprocating screen. The processes and equipment for preparing drug and carrier particles are disclosed in *Pharmaceutical Sciences*, Remington, 17th Ed., pp. 1585-1594 (1985); *Chemical Engineers Handbook*, Perry, 6th Ed., pp. 21-13 to 21-19 (1984); *Journal of Pharmaceutical Sciences*, Parrot, Vol. 61, No. 6, pp. 813-829 (1974); and *Chemical Engineer*, Hixon, pp. 94-103 (1990).

First drug layer 30 comprises paliperidone in an admixture with selected excipients adapted to provide an osmotic activity gradient for driving fluid from an external environment through membrane 20 and for forming a deliverable drug formulation upon imbibition of fluid. The excipients may include a suitable suspending agent, also referred to herein as a drug carrier, and an osmotically active agent, i.e., an "osmagent," such as salt. Other excipients such as lubricants, binders, etc. may also be included. It has been surprisingly found that when first component drug layer 30 comprises an osmotically active component, and a lower amount of active drug than in second component drug layer 40, an improved ascending rate of release can be created that provides a longer duration of ascending rate. Additionally, with the low doses of paliperidone delivered from a dosage form, and the low amount of that total in the first drug layer 30, the addition of salt has been found to provide a consistent predetermined release rate providing a substantially ascending rate of release over 20 hours.

The osmotically active component in the first drug layer typically comprises an osmagent and one or more osmopolymer(s) having relatively small molecular weights which exhibit swelling as fluid is imbibed such that release of these osmopolymers through exit 60 occurs similar to that of drug layer 40.

First drug layer 30 may also comprise additional excipients such as binders, lubricants, antioxidants and colorants.

It has been surprisingly discovered that the ratio of drug concentration between the first drug layer and the second drug layer alters the release rate profile. Release rate profile slope is calculated as the difference between the maximum release rate and the release rate achieved at the first time point after start-up (for example, at 6 hours), divided by the average release rate between the two data points.

Figure 5:
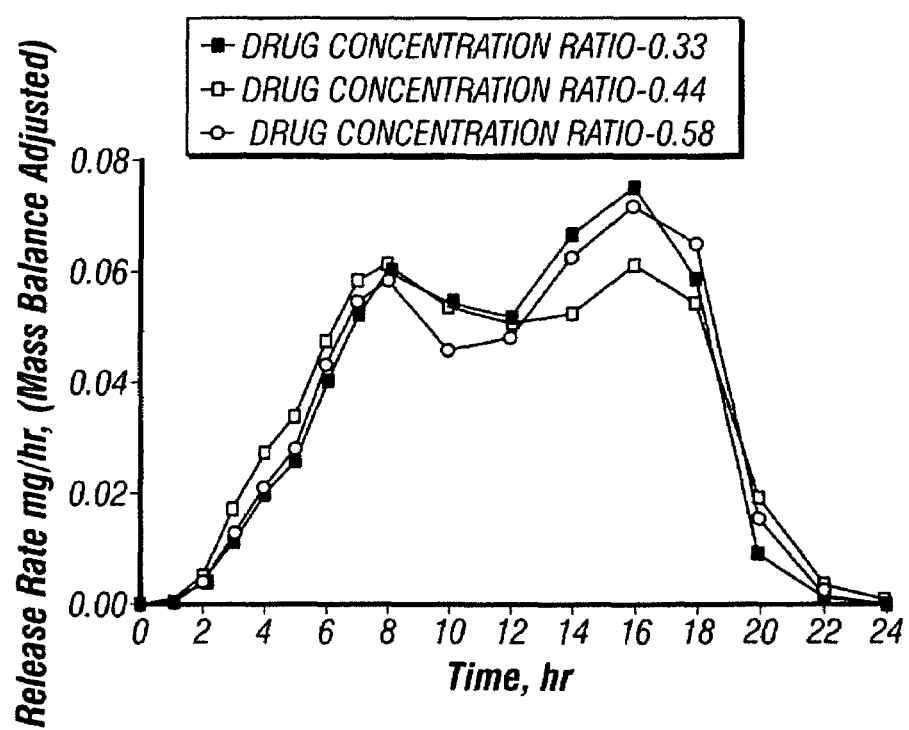
FIG. 5 illustrates the effect of drug concentration ratio between the first drug layer and the second drug layer on rate of release of paliperidone.

For instance, in Example 1, the drug concentration in first drug layer 30 is 1% and the drug concentration in the second drug layer 40 is 2.8% resulting in a 0.36 ratio of drug concentrations between the two layers that provides a 60% release rate profile. It has been found that the slope of the release rate profile can be manipulated by adjusting the ratio of drug concentrations between the two layers. High drug concentration ratio produces less ascending release rates as shown in FIG. 5. The drug concentration ratio to produce greater than 50% ascending release rate curve slope is less than 0.4.

Figure 4:
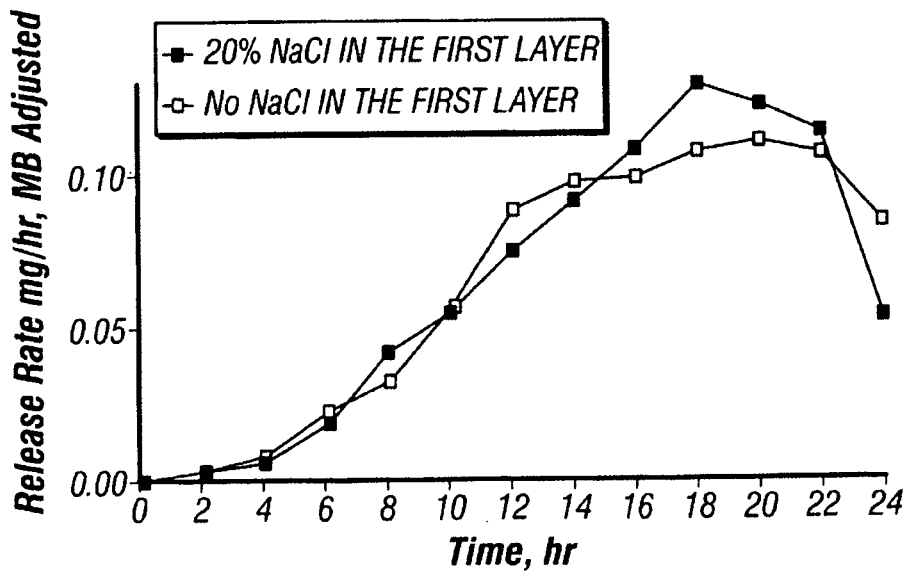
FIG. 4 illustrates the model delivery profile providing a substantially ascending rate of release of paliperidone demonstrating the effect of sodium chloride in the first drug layer.

Similarly, it has been found that reduced salt in the first drug layer 30 also reduces the release rate curve slope. For example when no salt is added the release rate curve slope is about 57. When 20% salt is added, the release rate curve slope increases to 80%. See FIG. 4. The amount of salt required to provide the preferred ascending release rate profile is at least 20%.

It has been surprisingly discovered that the ascending rate of release of paliperidone provides superior bioavailability, absorption and efficacy over multiple dosings of immediate release dosage forms as well as substantially zero order rates of release over prolonged periods of time.

Drug layer 30 and drug layer 40 may optionally contain surfactants and disintegrants in both drug layers. Exemplary of the surfactants are those having an HLB value of between about 10-25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate and the like. Disintegrants may be selected from starches, clays, celluloses, algins and gums and crosslinked starches, celluloses and polymers. Representative disintegrants include corn starch, potato starch, croscarmelose, crospovidone, sodium starch glycolate, Veegum HV, methylcellulose, agar, bentonite, carboxymethylcellulose, alginic acid, guar gum and the like.

Another representative compound having similar antipsychotic activity to paliperidone is risperidone, sold in immediate release forms as RISPERDAL® (risperidone).

Blood plasma concentrations in a subject may be determined by clinical assay to determine a correlation between tolerability and clinical effect and blood plasma concentrations of drug. The present invention provides for a period of delivery utilizing a substantially ascending blood plasma concentration profile.

Dosage forms of the present invention have core drug release $T_{90}$ values of greater than 8 hours, greater 12 hours, greater than 14, preferably greater than 16 hours and most preferably greater than 20 hours, and release paliperidone or risperidone for a continuous period of time of about 22 hours. After about one hour following administration, the dosage form begins releasing paliperidone or risperidone from the core at a substantially ascending rate of release that continues for a prolonged period of time of about 16 hours or more.

Wall 20 is formed to be permeable to the passage of an external fluid, such as water and biological fluids, and is substantially impermeable to the passage of paliperidone or risperidone, osmagent, osmopolymer and the like. As such, it is semipermeable. The selectively semipermeable compositions used for forming wall 20 are essentially nonerodible and substantially insoluble in biological fluids during the life of the dosage form.

Representative polymers for forming wall 20 comprise semipermeable homopolymers, semipermeable copolymers, and the like. Such materials comprise cellulose esters, cellulose ethers and cellulose ester-ethers. The cellulosic polymers have a degree of substitution (DS) of their anhydroglucose unit of from greater than 0 up to 3, inclusive. Degree of substitution (DS) means the average number of hydroxyl groups originally present on the anhydroglucose unit that are replaced by a substituting group or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkysulfamate, semipermeable polymer forming groups, and the like, wherein the organic moieties contain from one to twelve carbon atoms, and preferably from one to eight carbon atoms.

The semipermeable compositions typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di-, and tri-alkenylates, mono-, di-, and tri-aroylates, and the like. Exemplary polymers include cellulose acetate having a DS of 1.8 to 2.3 and an acetyl content of 32 to 39.9%; cellulose diacetate having a DS of 1 to 2 and an acetyl content of 21 to 35%; cellulose triacetate having a DS of 2 to 3 and an acetyl content of 34 to 44.8%; and the like. More specific cellulosic polymers include cellulose propionate having a DS of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a DS of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a DS of 2.6 to 3, such as cellulose trivalerate, cellulose trilamate, cellulose tripalmitate, cellulose trioctanoate and cellulose tripropionate; cellulose diesters having a DS of 2.2 to 2.6, such as cellulose disuccinate, cellulose dipalmitate, cellulose dioctanoate, cellulose dicaprylate, and the like; and mixed cellulose esters, such as cellulose acetate valerate, cellulose acetate succinate, cellulose propionate succinate, cellulose acetate octanoate, cellulose valerate palmitate, cellulose acetate heptanoate, and the like. Semipermeable polymers are known in U.S. Pat. No. 4,077,407, and they can be synthesized by procedures described in *Encyclopedia of Polymer Science and Technology*, Vol. 3, pp. 325-354 (1964), Interscience Publishers Inc., New York, N.Y.

Additional semipermeable polymers for forming wall 20 comprise cellulose acetaldehyde dimethyl acetate; cellulose acetate ethylcarbamate; cellulose acetate methyl carbamate; cellulose dimethylaminoacetate; semipermeable polyamide; semipermeable polyurethanes; semipermeable sulfonated polystyrenes; cross-linked selectively semipermeable polymers formed by the coprecipitation of an anion and a cation, as disclosed in U.S. Pat. Nos. 3,173,876; 3,276,586; 3,541,005; 3,541,006 and 3,546,142; semipermeable polymers, as disclosed by Loeb, et al. in U.S. Pat. No. 3,133,132; semipermeable polystyrene derivatives; semipermeable poly(sodium styrenesulfonate); semipermeable poly(vinylbenzyltrimethylammonium chloride); and semipermeable polymers exhibiting a fluid permeability of $10^{-5}$ to $10^{-2}$ (cc. mil/cm hr.atm), expressed as per atmosphere of hydrostatic or osmotic pressure differences across a semipermeable wall. The polymers are known to the art in U.S. Pat. Nos. 3,845,770; 3,916,899 and 4,160,020; and in *Handbook of Common Polymers*, Scott and Roff (1971) CRC Press, Cleveland, Ohio.

Wall 20 may also comprise a flux-regulating agent. The flux regulating agent is a compound added to assist in regulating the fluid permeability or flux through wall 20. The flux-regulating agent can be a flux-enhancing agent or a flux-decreasing agent. The agent can be preselected to increase or decrease the liquid flux. Agents that produce a marked increase in permeability to fluid such as water are often essentially hydrophilic, while those that produce a marked decrease to fluids such as water are essentially hydrophobic. The amount of regulator in the wall when incorporated therein generally is from about 0.01% to 20% by weight or more. The flux regulator agents may include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight glycols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; esters such as ethylene glycol dipropionate, ethylene glycol butyrate, butylene glycol dipropionate, glycerol acetate esters, and the like. Presently preferred flux enhancers include the group of difunctional block-copolymer polyoxyalkylene derivatives of propylene glycol known as pluronics (BASF). Representative flux-decreasing agents include phthalates substituted with an alkyl or alkoxy or with both an alkyl and alkoxy group such as diethyl phthalate, dimethoxyethyl phthalate, dimethyl phthalate, and [di(2-ethylhexyl)phthalate], aryl phthalates such as triphenyl phthalate, and butyl benzyl phthalate; insoluble salts such as calcium sulfate, barium sulfate, calcium phosphate, and the like; insoluble oxides such as titanium oxide; polymers in powder, granule and like form such as polystyrene, polymethylmethacrylate, polycarbonate, and polysulfone; esters such as citric acid esters esterified with long chain alkyl groups; inert and substantially water impermeable fillers; resins compatible with cellulose based wall forming materials, and the like.

Other materials may be included in the semipermeable wall composition for imparting flexibility and elongation properties, for making wall 20 less brittle and to render tear strength. Suitable materials include phthalate plasticizers such as dibenzyl phthalate, dihexyl phthalate, butyl octyl phthalate, straight chain phthalates of six to eleven carbons, di-isononyl phthalte, di-isodecyl phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in a wall when incorporated therein is about 0.01% to 20% weight, or higher.

Figure 3:
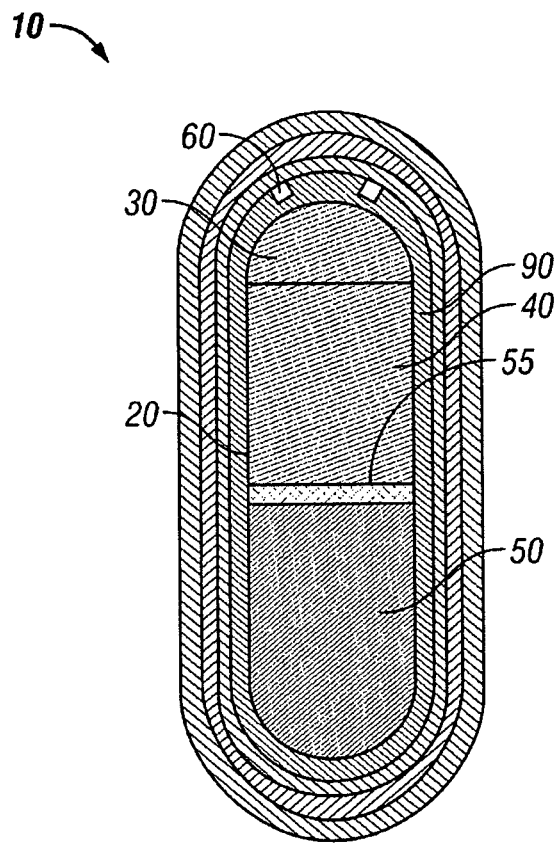
FIG. 3 illustrates an embodiment of the present invention prior to administration to a subject, with an optional lubricating subcoat and barrier layer.

Push layer 50, the third component, comprises an expandable composition in contacting layered arrangement with the second component drug layer 40 as illustrated in FIG. 1 or in contacting layered arrangement with barrier layer 55 as illustrated in FIG. 3. Push layer 50 comprises a polymer that imbibes an aqueous or biological fluid and swells to push the drug composition through the exit of the device. A polymer having suitable imbibition properties may be referred to herein as an osmopolymer. The osmopolymers are swellable, hydrophilic polymers that interact with water and aqueous biological fluids and swell or expand to a high degree, typically exhibiting a 2-50 fold volume increase. The osmopolymer can be non-crosslinked or crosslinked, but in a preferred embodiment are at least lightly crosslinked to create a polymer network that is too large and entangled to exit the dosage form. Thus, in a preferred embodiment, the expandable composition is retained within the dosage form during its operative lifetime.

Representatives of fluid-imbibing displacement polymers comprise members selected from poly(alkylene oxide) of 1 million to 15 million number-average molecular weight, as represented by poly(ethylene oxide), and poly(alkali carboxymethylcellulose) of 500,000 to 3,500,000 number-average molecular weight, wherein the alkali is sodium, potassium or lithium. Examples of additional polymers for the formulation of the push layer composition comprise osmopolymers that form hydrogels, such as Carbopol® acidic carboxypolymer, a polymer of acrylic cross-linked with a polyallyl sucrose, also known as carboxypolymethylene, and carboxyvinyl polymer having a molecular weight of 250,000 to 4,000,000; CYANAMER® polyacrylamides; cross-linked water swellable indenemaleic anhydride polymers; GOOD RITE® polyacrylic acid having a molecular weight of 80,000 to 200,000; AQUA KEEPS® acrylate polymer polysaccharides composed of condensed glucose units, such as diester cross-linked polygluran; and the like. Representative polymers that form hydrogels are known to the prior art in U.S. Pat. No. 3,865,108, issued to Hartop; U.S. Pat. No. 4,002,173, issued to Manning; U.S. Pat. No. 4,207,893, issued to Michaels; and in *Handbook of Common Polymers*, Scott and Roff, Chemical Rubber Co., Cleveland, OH.

Suitable osmagents, also known as osmotic solutes and osmotically effective agents, that may be found in the first drug layer and the push layer in the dosage form are those which exhibit an osmotic activity gradient across the wall 20. Suitable osmagents comprise a member selected from the group consisting of sodium chloride, potassium chloride, lithium chloride, magnesium sulfate, magnesium chloride, potassium sulfate, sodium sulfate, lithium sulfate, potassium acid phosphate, mannitol, urea, inositol, magnesium succinate, tartaric acid, raffinose, sucrose, glucose, lactose, sorbitol, inorganic salts, organic salts and carbohydrates.

Exemplary solvents suitable for manufacturing the dosage form components comprise aqueous or inert organic solvents that do not adversely harm the materials used in the system. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride nitroethane, nitropropane tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium chloride, calcium chloride, and the like, and mixtures thereof such as acetone and water, acetone and methanol, acetone and ethyl alcohol, methylene dichloride and methanol, and ethylene dichloride and methanol.

FIG. 3 illustrates an alternate embodiment including an optional third component barrier layer 55 separating second component drug layer 40 from push layer 50. FIG. 3 also illustrates dosage form 10 including an inner wall 90.

FIG. 3 illustrates the preferred embodiment of dosage form 10 including the protective inner wall or subcoat 90 and an optional third component barrier layer 55 separating second component drug layer 40 from push layer 50.

The composition of barrier layer 55 is inert with the respect to the composition of second component drug layer 40 and substantially impermeable; such that drug from drug layer 40 and the components of push layer 50 are prevented from mixing. Suitable materials include water-insoluble polymers, fats, fatty acids and fatty acid esters that are solids at ambient and body temperatures, and waxes. Representative water-insoluble polymers include ethyl cellulose, cellulose acetate, polyvinylchloride, copolymers of polyethylene and vinyl acetate, poly(methylmethacrylate), acrylic polymers such as EURDRAGIT® L or EURDRAGIT® R, polycaprolactone, poly(lactic-co-glycolic) acid polymers (PLGA), high density polyethylene, rubber, styrene butadiene, polysilicone, nylon, , polystyrene, polytetrafluoroethylene, and halogenated polymers. Representative waxes include paraffin wax and beeswax. Representative fats, fatty acids and fatty acid esters include $C_{16}$-$C_{24}$ long chain fatty acids, esters of such long chain fatty acids such as stearic acid and oleic acid, and mixtures of the foregoing. Mixtures of the above-described materials may be utilized, e.g., a mixture of ethyl cellulose and stearic acid, which is presently preferred.

Protective subcoat 90 is permeable to the passage of gastric fluid entering the compartment defined by wall 20 and provides a protective function that reduces the degradation of paliperidone under stress conditions.

Inner wall 90 further provides a lubricating function that facilitates the movement of first drug layer 30, second drug layer 40 and push layer 50 toward exit 60. Inner wall 90 may be formed from hydrophilic materials and excipients. Outer wall 20 is semipermeable, allowing gastric fluid to enter the compartment, but preventing the passage of the materials comprising the core in the compartment. The deliverable drug formulation is released from exit 60 as described above with respect to the embodiment of FIG. 3.

Figure 7:
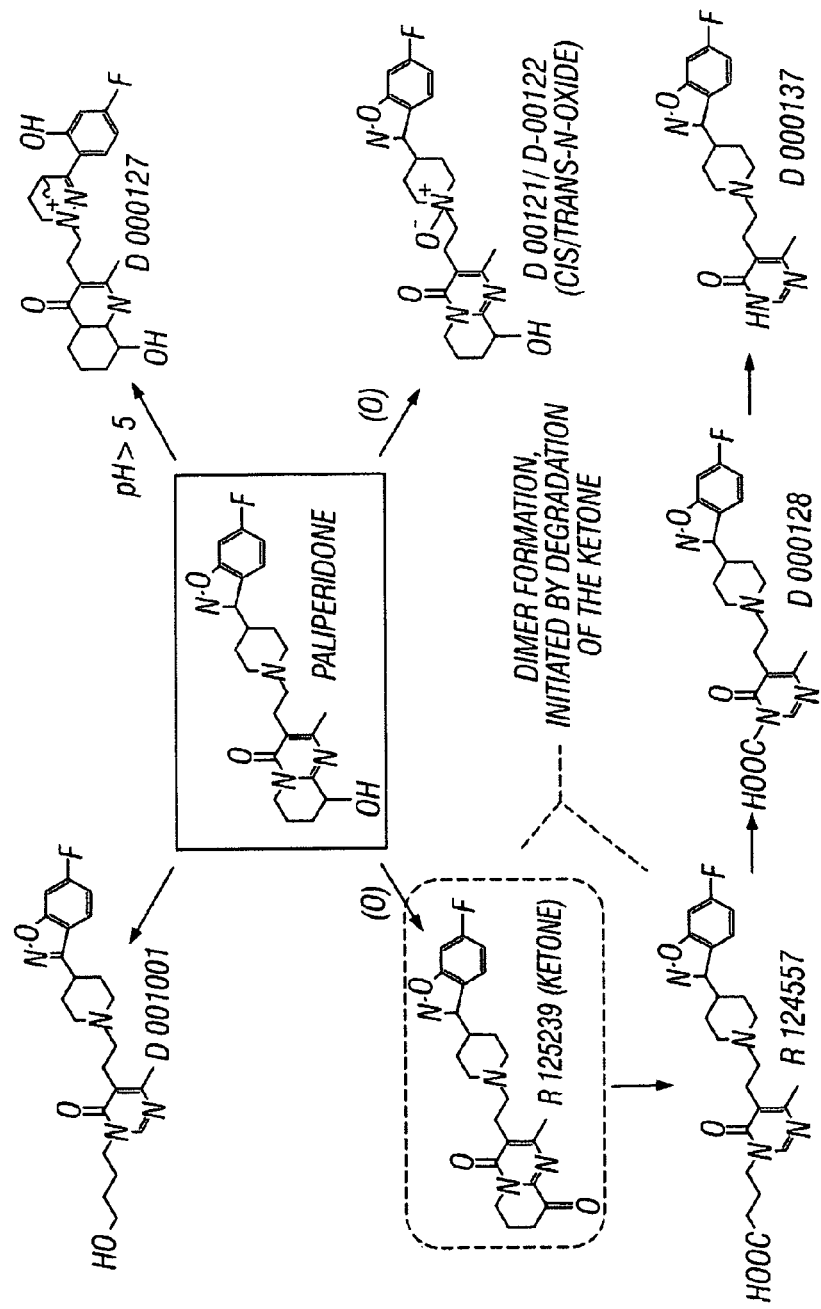
FIG. 7 illustrates potential degradation pathways for paliperidone under stress conditions.

FIG. 7 illustrates potential degradation pathways for paliperidone under stress conditions. Subcoat 90 provides a means for reducing this potential degradation.

Inner wall 90 may be formed from hydrophilic materials and excipients. Wall 20 is semipermeable, allowing gastric fluid to enter the compartment, but substantially impermeable to the passage of materials comprising the core in the compartment. The deliverable drug formulation is released from exit 60 as described above with respect to the embodiment of FIG. 3.

Inner wall 90, is located between at least drug layers 30 and 40, and wall 20 to reduce degradation of the active agent of drug layer 30 and drug layer 40. Inner wall 90 promotes stability of the drug composition.

Inner wall 90 also reduces friction between the external surface of drug layer 30 and drug layer 40, and the inner surface of wall 20. Inner wall 90 promotes release of the drug composition from the compartment and reduces the amount of residual drug composition remaining in the compartment at the end of the delivery period, particularly when the slurry, suspension or solution of the drug composition that is being dispensed is highly viscous during the period of time in which it is being dispensed. In dosage forms in which there is high drug loading, i.e., 40% or greater active agent in the drug layer based on the overall weight of the drug layer, and no inner wall, it has been observed that significant residual amounts of drug may remain in the device after the period of delivery has been completed. In some instances, amounts of 20% or greater may remain in the dosage form at the end of a twenty-four hour period when tested in a release rate assay.

Inner wall 90 is formed as an inner coat of a flow-promoting agent, i.e., an agent that lowers the frictional force between the outer wall 20 and the external surface of drug layer 40. Inner wall 90 appears to reduce the frictional forces between outer wall 20 and the outer surface of drug layer 30 and drug layer 40, thus allowing for more complete delivery of drug from the device. Particularly in the case of active compounds having a high cost, such an improvement presents substantial economic advantages since it is not necessary to load the drug layer with an excess of drug to insure that the minimum amount of drug required will be delivered. Inner wall 90 may be formed as a coating applied over the compressed core.

Inner wall 90 is further characterized by a protective agent, i.e., an agent that reduces the degradation of paliperidone in drug layer 30 and drug layer 40. Particularly in the case of active compounds having a high cost, such an improvement presents substantial economic advantages. Inner wall 90 may be formed as a coating applied over the compressed core.

Inner wall 90 typically may be 0.01 to 5 mm thick, more typically 0.5 to 5 mm thick, and it comprises a member selected from hydrogels, gelatin, low molecular weight polyethylene oxides, e.g., less than 100,000 MW, hydroxyalkylcelluloses, e.g., hydroxyethylcellulose, hydroxypropylcellulose, hydroxyisopropylcellulose, hydroxybutylcellulose and hydroxyphenylcellulose, and hydroxyalkyl alkylcelluloses, e.g., hydroxypropyl methylcellulose, and mixtures thereof. The hydroxyalkylcelluloses comprise polymers having a 9,500 to 1,250,000 number-average molecular weight. For example, hydroxypropyl celluloses having number average molecular weights of between 80,000 to 850,000 are useful. The inner wall may be prepared from conventional solutions or suspensions of the aforementioned materials in aqueous solvents or inert organic solvents.

Preferred materials for the inner wall include hydroxypropyl cellulose, hydroxyethyl cellulose, hydroxypropyl methyl cellulose, povidone [poly(vinylpyrrolidone)], polyethylene glycol, and mixtures thereof.

Most preferred are mixtures of hydroxypropyl cellulose and povidone, prepared in organic solvents, particularly organic polar solvents such as lower alkanols having 1-8 carbon atoms, preferably ethanol, mixtures of hydroxyethyl cellulose and hydroxypropyl methyl cellulose prepared in aqueous solution, and mixtures of hydroxyethyl cellulose and polyethylene glycol prepared in aqueous solution. More preferably, the inner wall comprises a mixture of hydroxypropyl cellulose and providone prepared in ethanol. Most preferably the inner wall comprises a mixture of hydrxoyethylcellulose and polyethylene prepared in water.

It is preferred that inner wall 90 comprises between about 50% and about 90% hydroxypropylcellulose identified as EF having an average molecular weight of about 80,000 and between about 10% and about 50% polyvinylpyrrolidone identified as K29-32. In another embodiment it is preferred that the inner wall 90 comprises between about 50% and about 98% hydroxyethylcelluose identified as NATROSOL 250 L having an average molecular weight of about 90,000 and between about 2% and about 50% polyethylene glycol identified a as 3350 having molecular weight of between about 3,000 and 4,000.

Conveniently, the weight of the inner wall applied to the compressed core may be correlated with the thickness of the inner wall and residual drug remaining in a dosage form in a release rate assay such as described herein. As such, during manufacturing operations, the thickness of the inner wall may be controlled by controlling the weight of the inner wall taken up in the coating operation.

When inner wall 90 is formed as a subcoat, i.e., by coating onto the tabletted composite including one or all of the first drug layer, second drug layer and push layer, the inner wall can fill in surface irregularities formed on the core by the tabletting process. The resulting smooth external surface facilitates slippage between the coated composite core and the semipermeable wall during dispensing of the drug, resulting in a lower amount of residual drug composition remaining in the device at the end of the dosing period. When inner wall 90 is fabricated of a gel-forming material, contact with water in the environment of use facilitates formation of the gel or gel-like inner coat having a viscosity that may promote and enhance slippage between outer wall 20 and drug layer 30 and drug layer 40.

Subcoat 90 has also been shown to reduce degradation of the paliperidone during stability testing and could improve and extend shelf life of the resulting formulation.

Figure 9A:
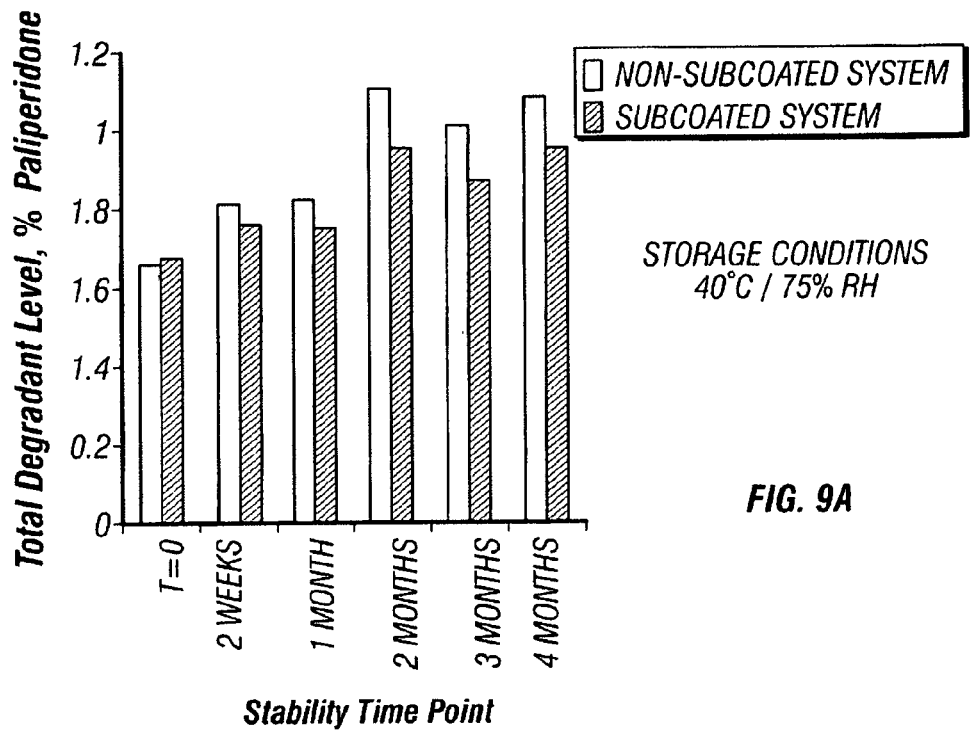
FIGS. 9A and 9B illustrate graphical comparison of dosage form stability with and without use of the protective subcoat of the present invention.
Figure 9B:
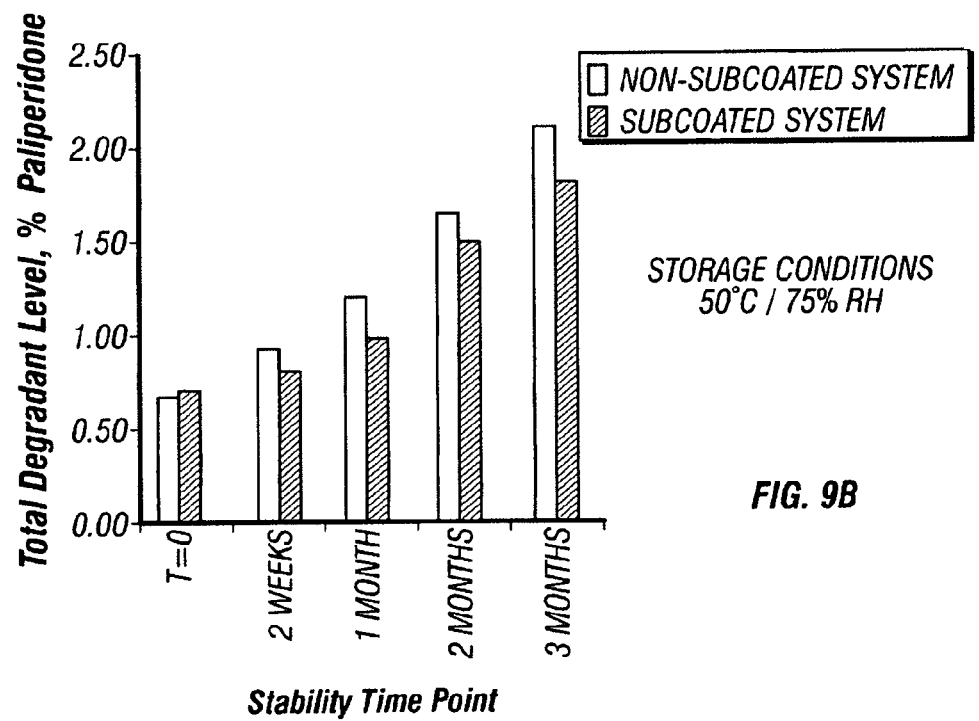

FIGS. 8, 9A and 9B illustrate the increased stability of paliperidone in the dosage forms incorporating the protective subcoat compared to dosage forms not incorporating the protective subcoat.

Pan coating may be conveniently used to provide the completed dosage form, except for the exit orifice. In the pan coating system, the wall-forming composition for the inner wall or the outer wall, as the case may be, is deposited by successive spraying of the appropriate wall composition onto the compressed trilayered or multilayered core comprising the drug layers, optional barrier layer and push layer, accompanied by tumbling in a rotating pan. A pan coater is used because of its availability at commercial scale. Other techniques can be used for coating the compressed core. Once coated, the wall is dried in a forced-air oven or in a temperature and humidity controlled oven to free the dosage form of solvent(s) used in the manufacturing. Drying conditions will be conventionally chosen on the basis of available equipment, ambient conditions, solvents, coatings, coating thickness, and the like.

Other coating techniques can also be employed. For example, the wall or walls of the dosage form may be formed in one technique using the air-suspension procedure_ This procedure consists of suspending and tumbling the compressed core in a current of air and the semipermeable wall forming composition, until the wall is applied to the core. The air-suspension procedure is well suited for independently forming the wall of the dosage form. The air-suspension procedure is described in U.S. Pat. No. 2,799,241; in *J. Am. Pharm. Assoc.*, Vol. 48, pp. 451-459 (1959); and, ibid., Vol.

49, pp. 82-84 (1960). The dosage form also can be coated with a Wurster air-suspension coater using, for example, methylene dichloride methanol as a cosolvent for the wall forming material. An AEROMATIC® air-suspension coater can be used employing a cosolvent.

Dosage forms in accord with the present invention are manufactured by standard techniques. For example, the dosage form may be manufactured by the wet granulation technique. In the wet granulation technique, the drug and carrier are blended using an organic solvent, such as denatured anhydrous ethanol, as the granulation fluid. The remaining ingredients can be dissolved in a portion of the granulation fluid, such as the solvent described above, and this latter prepared wet blend is slowly added to the drug blend with continual mixing in the blender. The granulating fluid is added until a wet blend is produced, which wet mass blend is then forced through a predetermined screen onto oven trays. The blend is dried for 18 to 24 hours at 24° C. to 35° C. in a forced-air oven. The dried granules are then sized. Next, magnesium stearate, or another suitable lubricant, is added to the drug granulation, and the granulation is put into milling jars and mixed on a jar mill for 10 minutes. The composition is pressed into a layer, for example, in a Manesty press or a Korsch LCT press. For a trilayered core, granules or powders of the drug layer compositions and push layer composition are sequentially placed in an appropriately-sized die with intermediate compression steps being applied to each of the first two layers, followed by a final compression step after the last layer is added to the die to form the trilayered core. The intermediate compression typically takes place under a force of about 50-100 newtons. Final stage compression typically takes place at a force of 3500 newtons or greater, often 3500-5000 newtons. The compressed cores are fed to a dry coater press, e.g., Kilian Dry Coater press, and subsequently coated with the wall materials as described above.

One or more exit orifices are drilled in the drug layer end of the dosage form, and optional water soluble overcoats, which may be colored (e.g., OPADRY® colored coatings) or clear (e.g., OPADRY® Clear), may be coated on the dosage form to provide the finished dosage form.

In another manufacture the drug and other ingredients comprising the drug layer are blended and pressed into a solid layer. The layer possesses dimensions that correspond to the internal dimensions of the area the layer is to occupy in the dosage form, and it also possesses dimensions corresponding to the push layer, if included, for forming a contacting arrangement therewith. The drug and other ingredients can also be blended with a solvent and mixed into a solid or semisolid form by conventional methods, such as ballmilling, calendering, stirring or rollmilling, and then pressed into a preselected shape. Next, if included, a layer of osmopolymer composition is placed in contact with the layer of drug in a like manner. The layering of the drug formulation and the osmopolymer layer can be fabricated by conventional two-layer press techniques. An analogous procedure may be followed for the preparation of the trilayered core. The compressed cores then may be coated with the inner wall material and the semipermeable wall material as described above.

Another manufacturing process that can be used comprises blending the powdered ingredients for each layer in a fluid bed granulator. After the powdered ingredients are dry blended in the granulator, a granulating fluid, for example, poly(vinylpyrrolidone) in water, is sprayed onto the powders. The coated powders are then dried in the granulator. This process granulates all the ingredients present therein while adding the granulating fluid. After the granules are dried, a lubricant, such as stearic acid or magnesium stearate, is mixed into the granulation using a blender e.g., V-blender or tote blender. The granules are then pressed in the manner described above.

The dosage form of the invention is provided with at least one exit 60. Exit 60 cooperates with the compressed core for the uniform release of drug from the dosage form. The exit can be provided during the manufacture of the dosage form or during drug delivery by the dosage form in a fluid environment of use.

Exit 60 may include an orifice that is formed or formable from a substance or polymer that erodes, dissolves or is leached from the outer wall to thereby form an exit orifice. The substance or polymer may include, for example, an erodible poly(glycolic) acid or poly(lactic) acid in the semipermeable wall; a gelatinous filament; a water-removable poly (vinyl alcohol); a leachable compound, such as a fluid removable pore-former selected from the group consisting of inorganic and organic salt, oxide and carbohydrate.

An exit, or a plurality of exits, can be formed by leaching a member selected from the group consisting of sorbitol, lactose, fructose, glucose, mannose, galactose, talose, sodium chloride, potassium chloride, sodium citrate and mannitol to provide a uniform-release dimensioned pore-exit orifice.

The exit can have any shape, such as round, triangular, square, elliptical and the like for the uniform metered dose release of a drug from the dosage form.

The dosage form can be constructed with one or more exits in spaced-apart relation or one or more surfaces of the dosage form.

Drilling, including mechanical and laser drilling, through the semipermeable wall can be used to form the exit orifice. Such exits and equipment for forming such exits are disclosed in U.S. Pat. Nos. 3,916,899, by Theeuwes and Higuchi and in U.S. Pat. No. 4,088,864, by Theeuwes, et al. It is presently preferred to utilize two exits of equal diameter.

Dosage forms of this invention exhibit sustained release of drug over a continuous time period that includes a prolonged time when drug is released at an ascending release rate as determined in a standard release rate assay such as that described herein. When administered to a subject, the dosage forms of the invention provide substantially ascending blood plasma drug concentrations in the subject that are less variable over a prolonged period of time than those obtained with immediate release dosage forms. When the dosage forms of this invention are administered on a continuous once-a-day basis, the dosage forms of the invention provide therapeutically effective ascending plasma drug concentrations while providing steady-state peak plasma drug concentrations that occur at a later time following dose administration and that exhibit a lesser magnitude than the steady-state peak plasma drug concentrations that occur following twice or three times a day administration of an immediate-release dosage form.

The practice of the foregoing methods of orally administering a dosage form to a subject once a day is preferred. The mg of compound delivered in a dosage form to the patient may be from 0.25 to about 20 mg (e.g. 0.25 mg, 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, and 20 mg) per oral dosage form. Other disease states and conditions, which may be manifested or diagnosed as requiring an antipsychotic, may be treated with the paliperidone or risperidone dosage forms and methods of the invention. In addition, other disease states and conditions which may or may not manifest in association with depression or anxiety, but which may be responsive to treatment with paliperidone or risperidone may also be treated with the dosage forms and methods of the invention.

Preferred methods of manufacturing dosage forms of the present invention are generally described below. All percentages are weight percent unless otherwise noted.

EXAMPLE 1

Paliperidone Capsule Shaped Tablet, Trilayer 1.9 mg System

A dosage form adapted, designed and shaped as an osmotic drug delivery device is manufactured as follows: 100 g of paliperidone, 7345 g of polyethylene oxide with average molecular weight of 200,000, and 2000 g of sodium chloride, USP are added to a fluid bed granulator bowl. Next a binder solution is prepared by dissolving 800 g of hydroxypropylmethyl cellulose identified as 2910 having an average viscosity of 5 cps in 9,200 g of water. The dry materials are fluid bed granulated by spraying with 6750 g of binder solution. Next, the wet granulation is dried in the granulator to an acceptable moisture content, and sized using by passing through a 7-mesh screen. Next, the granulation is transferred to a blender and mixed with 5 g of butylated hydroxytoluene as an antioxidant and lubricated with 50 g of stearic acid.

Next, a second drug compartment composition is prepared as follows: 280 g of paliperidone and 9165 g of polyethylene oxide with average molecular weight of 200,000 are added to a fluid bed granulator bowl. Next a binder solution is prepared by dissolving 800 g of hydroxypropylmethyl cellulose identified as 2910 having an average viscosity of 5 cps in 9,200 g of water. The dry materials are fluid bed granulated by spraying with 6750 g of binder solution. Next, the wet granulation is dried in the granulator to an acceptable moisture content, and sized using by passing through a 7-mesh screen. Next, the granulation is transferred to a blender and mixed with 5 g of butylated hydroxytoluene as an antioxidant and lubricated with 50 g of stearic acid.

Next, a push composition is prepared as follows: first, a binder solution is prepared. 15.6 kg of polyvinylpyrrolidone identified as K29-32 having an average molecular weight of 40,000 is dissolved in 104.4 kg of water. Then, 24 kg of sodium chloride and 1.2 kg of ferric oxide are sized using a Quadro Comil with a 21-mesh screen. Then, the screened materials and 88.44 kg of Polyethylene oxide (approximately 7,000,000 molecular weight) are added to a fluid bed granulator bowl. The dry materials are fluidized and mixed while 46.2 kg of binder solution is sprayed from 3 nozzles onto the powder. The granulation is dried in the fluid-bed chamber to an acceptable moisture level. The coated granules are sized using a Fluid Air mill with a 7-mesh screen. The granulation is transferred to a tote tumbler, mixed with 15 g of butylated hydroxytoluene and lubricated with 294 g magnesium stearate.

Next, the paliperidone drug compositions for the first and the second compartments and the push composition are compressed into trilayer tablets. First, 50 mg of the paliperidone compartment one composition is added to the die cavity and pre-compressed, then 50 mg of the paliperidone compartment two composition is added to the die cavity and pre-compressed, then 110 mg of the push composition is added and the layers are pressed into a 3/16" diameter longitudinal, deep concave, trilayer arrangement.

The trilayered arrangements are coated with a subcoat laminate. The wall forming composition comprises 70% hydroxypropyl cellulose identified as EF, having an average molecular weight of 80,000 and 30% of polyvinylpyrrolidone identified as K29-32 having an average molecular weight of 40,000. The wall-forming composition is dissolved in anhydrous ethyl alcohol, to make an 8% solids solution. The wall-forming composition is sprayed onto and around the bilayered arrangements in a pan coater until approximately 20 mg of laminate is applied to each tablet.

The trilayered arrangements are coated with a semi-permeable wall. The wall forming composition comprises 99% cellulose acetate having a 39.8% acetyl content and 1% polyethylene glycol comprising a 3.350 viscosity-average molecular weight. The wall-forming composition is dissolved in an acetone:water (95:5 wt:wt) co solvent to make a 5% solids solution. The wall-forming composition is sprayed onto and around the bilayered arrangements in a pan coater until approximately 45 mg of membrane is applied to each tablet.

Next, two 25 mil (0.6 mm) exit passageways are laser drilled through the semi-permeable wall to connect the drug layer with the exterior of the dosage system. The residual solvent is removed by drying for 144 hours as 45 C. and 45% humidity. After drilling, the osmotic systems are dried for 4 hours at 45 C. to remove excess moisture.

The dosage form produced by this manufacture is designed to deliver 1.9 mg of paliperidone in an ascending delivery pattern from two drug-containing cores. First core contains 1% paliperidone, 73.45% polyethylene oxide possessing a 200,000 molecular weight, 20% sodium chloride, USP, 5% hydroxypropylmethyl cellulose having an average viscosity of 5 cps, 0.05% butylated hydroxytoluene, and 0.5% stearic acid. Second drug core contains 2.8% paliperidone, 91.65% polyethylene oxide possessing a 200,000 molecular weight, 5% hydroxypropylmethyl cellulose having an average viscosity of 5 cps, 0.05% butylated hydroxytoluene, and 0.5% stearic acid. The push composition is comprised 73.7% polyethylene oxide comprising a 7,000,000 molecular weight, 20% sodium chloride, 5% polyvinylpyrrolidone possessing an average molecular weight of 40,000, 1% ferric oxide, 0.05% butylated hydroxytoluene, and 0.25% magnesium stearate. The semi permeable wall is comprised of 99% cellulose acetate of 39.8% acetyl content and 1% polyethylene glycol. The dosage form comprises two passageways, 25 mils (0.6 mm) on the center of the drug side.

EXAMPLE 2

Paliperidone Capsule Shaped Tablet, Trilayer 0.5 mg System

A dosage form adapted, designed and shaped as an osmotic drug delivery device is manufactured as follows: 25 g of paliperidone, 7420 g of polyethylene oxide with average molecular weight of 200,000, and 2000 g of sodium chloride, USP are added to a fluid bed granulator bowl. Next a binder solution is prepared by dissolving 800 g of hydroxypropylmethyl cellulose identified as 2910 having an average viscosity of 5 cps in 9,200 g of water. The dry materials are fluid bed granulated by spraying with 6750 g of binder solution. Next, the wet granulation is dried in the granulator to an acceptable moisture content, and sized using by passing through a 7-mesh screen. Next, the granulation is transferred to a blender and mixed with 5 g of butylated hydroxytoluene as an antioxidant and lubricated with 50 g of stearic acid.

Next, a second drug compartment composition is prepared as follows: 70 g of paliperidone and 9375 g of polyethylene oxide with average molecular weight of 200,000 are added to a fluid bed granulator bowl. Next a binder solution is prepared by dissolving 800 g of hydroxypropylmethyl cellulose identified as 2910 having an average viscosity of 5 cps in 9,200 g of water. The dry materials are fluid bed granulated by spraying with 6750 g of binder solution. Next, the wet granulation is dried in the granulator to an acceptable moisture content, and sized using by passing through a 7-mesh screen. Next, the granulation is transferred to a blender and mixed with 5 g of butylated hydroxytoluene as an antioxidant and lubricated with 50 g of stearic acid.

Next, a push composition is prepared as follows: first, a binder solution is prepared. 15.6 kg of polyvinylpyrrolidone identified as K29-32 having an average molecular weight of 40,000 is dissolved in 104.4 kg of water. Then, 24 kg of sodium chloride and 1.2 kg of ferric oxide are sized using a Quadro Comil with a 21-mesh screen. Then, the screened materials and 88.44 kg of Polyethylene oxide (approximately 7,000,000 molecular weight) are added to a fluid bed granulator bowl. The dry materials are fluidized and mixed while 46.2 kg of binder solution is sprayed from 3 nozzles onto the powder. The granulation is dried in the fluid-bed chamber to an acceptable moisture level. The coated granules are sized using a Fluid Air mill with a 7-mesh screen. The granulation is transferred to a tote tumbler, mixed with 15 g of butylated hydroxytoluene and lubricated with 294 g magnesium stearate.

Next, the paliperidone drug compositions for the first and the second compartments and the push composition are compressed into trilayer tablets. First, 50 mg of the paliperidone compartment one composition is added to the die cavity and pre-compressed, then 50 mg of the paliperidone compartment two composition is added to the die cavity and pre-compressed, then 110 mg of the push composition is added and the layers are pressed into a 3/16" diameter longitudinal, deep concave, trilayer arrangement.

The trilayered arrangements are coated with a subcoat laminate. The wall forming composition comprises 70% hydroxypropyl cellulose identified as EF, having an average molecular weight of 80,000 and 30% of polyvinylpyrrolidone identified as K29-32 having an average molecular weight of 40,000. The wall-forming composition is dissolved in anhydrous ethyl alcohol, to make an 8% solids solution. The wall-forming composition is sprayed onto and around the bilayered arrangements in a pan coater until approximately 20 mg of laminate is applied to each tablet.

The trilayered arrangements are coated with a semi-permeable wall. The wall forming composition comprises 99% cellulose acetate having a 39.8% acetyl content and 1% polyethylene glycol comprising a 3.350 viscosity-average molecular weight. The wall-forming composition is dissolved in an acetone:water (95:5 wt:wt) co solvent to make a 5% solids solution. The wall-forming composition is sprayed onto and around the bilayered arrangements in a pan coater until approximately 39 mg of membrane is applied to each tablet.

Next, two 25 mil (0.6 mm) exit passageways are laser drilled through the semi-permeable wall to connect the drug layer with the exterior of the dosage system. The residual solvent is removed by drying for 144 hours as 45 C. and 45% humidity. After drilling, the osmotic systems are dried for 4 hours at 45 C to remove excess moisture.

The dosage form produced by this manufacture is designed to deliver 0.25 mg of paliperidone in an ascending delivery pattern from two drug-containing cores. First core contains 0.25% paliperidone, 74.20% polyethylene oxide possessing a 200,000 molecular weight, 20% sodium chloride, USP, 5% hydroxypropylmethyl cellulose having an average viscosity of 5 cps, 0.05% butylated hydroxytoluene, and 0.5% stearic acid. Second drug core contains 0.7% paliperidone, 93.75% polyethylene oxide possessing a 200,000 molecular weight, 5% hydroxypropylmethyl cellulose having an average viscosity of 5 cps, 0.05% butylated hydroxytoluene, and 0.5% stearic acid. The push composition is comprised 73.7% polyethylene oxide comprising a 7,000,000 molecular weight, 20% sodium chloride, 5% polyvinylpyrrolidone possessing an average molecular weight of 40,000, 1% ferric oxide, 0.05% butylated hydroxytoluene, and 0.25% magnesium stearate. The subcoat is comprised of 70% hydroxypropyl cellulose and 30% polyvinylpyrrolidone. The semi permeable wall is comprised of 99% cellulose acetate of 39.8% acetyl content and 1% polyethylene glycol. The dosage form comprises two passageways, 25 mils (0.6 mm) on the center of the drug side.

EXAMPLE 3

Paliperidone Capsule Shaped Tablet, Trilayer 15 mg System

A dosage form adapted, designed and shaped as an osmotic drug delivery device was manufactured as follows: 900 g of paliperidone, 6544 g of polyethylene oxide with average molecular weight of 200,000, and 2000 g of sodium chloride, USP were added to a fluid bed granulator bowl. Next a binder solution was prepared by dissolving 800 g of polyvinylpyrrolidone identified as K29-32 having an average molecular weight of 40,000 in 9,200 g of water. The dry materials were fluid bed granulated by spraying with 6750 g of binder solution. Next, the wet granulation was dried in the granulator to an acceptable moisture content, and sized using by passing through a 7-mesh screen. Next, the granulation was transferred to a blender and mixed with 5 g of butylated hydroxytoluene as an antioxidant and lubricated with 50 g of stearic acid.

Next, a second drug compartment composition was prepared as follows: 2100 g of paliperidone and 7345 g of polyethylene oxide with average molecular weight of 200,000 were added to a fluid bed granulator bowl. Next a binder solution was prepared by dissolving 800 g of polyvinylpyrrolidone identified as K29-32 having an average molecular weight of 40,000 in 9,200 g of water. The dry materials were fluid bed granulated by spraying with 6750 g of binder solution. Next, the wet granulation was dried in the granulator to an acceptable moisture content, and sized using by passing through a 7-mesh screen. Next, the granulation was transferred to a blender and mixed with 5 g of butylated hydroxytoluene as an antioxidant and lubricated with 50 g of stearic acid.

Next, a push composition was prepared as follows: first, a binder solution was prepared. 15.6 kg of polyvinylpyrrolidone identified as K29-32 having an average molecular weight of 40,000 was dissolved in 104.4 kg of water. Then, 24 kg of sodium chloride and 1.2 kg of ferric oxide were sized using a Quadro Comil with a 21-mesh screen. Then, the screened materials and 88.44 kg of Polyethylene oxide (approximately 7,000,000 molecular weight) were added to a fluid bed granulator bowl. The dry materials were fluidized and mixed while 46.2 kg of binder solution was sprayed from 3 nozzles onto the powder. The granulation was dried in the fluid-bed chamber to an acceptable moisture level. The coated granules were sized using a Fluid Air mill with a 7-mesh screen. The granulation was transferred to a tote tumbler, mixed with 15 g of butylated hydroxytoluene and lubricated with 294 g magnesium stearate.

Next, the paliperidone drug compositions for the first and the second compartments and the push composition were compressed into trilayer tablets. First, 50 mg of the paliperidone compartment one composition is added to the die cavity and pre-compressed, then 50 mg of the paliperidone compartment two composition was added to the die cavity and pre-compressed, then 100 mg of the push composition was added and the layers were pressed into a 3/16" diameter longitudinal, deep concave, trilayer arrangement.

The trilayered arrangements were coated with a subcoat laminate. The wall forming composition comprises 95% hydroxyethylcellulose and 5% of polyethylene glycol comprising a 3,350 viscosity-average molecular weight. The wall-forming composition was dissolved in water, to make an 8% solids solution. The wall-forming composition was sprayed onto and around the bilayered arrangements in a pan coater until approximately 10 mg of laminate was applied to each tablet.

The trilayered arrangements were coated with a semi-permeable wall. The wall forming composition comprises 99% cellulose acetate having a 39.8% acetyl content and 1% polyethylene glycol comprising a 3.350 viscosity-average molecular weight. The wall-forming composition was dissolved in an acetone:water (95:5 wt:wt) co solvent to make a 5% solids solution. The wall-forming composition was sprayed onto and around the bilayered arrangements in a pan coater until approximately 45 mg of membrane was applied to each tablet.

Next, two 25 mil (0.6 mm) exit passageways were laser drilled through the semi-permeable wall to connect the drug layer with the exterior of the dosage system. The residual solvent was removed by drying for 144 hours as 45 C. and 45% humidity. After drilling, the osmotic systems were dried for 4 hours at 45 C. to remove excess moisture.

The dosage form produced by this manufacture was designed to deliver 15 mg of paliperidone in an ascending delivery pattern from two drug-containing cores. First core contained 9% paliperidone, 65.44% polyethylene oxide possessing a 200,000 molecular weight, 20% sodium chloride, USP, 5% polyvinylpyrrolidone identified as K29-32 having an average molecular weight of 40,000, 0.05% butylated hydroxytoluene, and 0.5% stearic acid. Second drug core contained 21% paliperidone, 73.45% polyethylene oxide possessing a 200,000 molecular weight, 5% polyvinylpyrrolidone identified as K29-32 having an average molecular weight of 40,000, 0.05% butylated hydroxytoluene, and 0.5% stearic acid. The push composition was comprised 73.7% polyethylene oxide comprising a 7,000,000 molecular weight, 20% sodium chloride, 5% polyvinylpyrrolidone possessing an average molecular weight of 40,000, 1% ferric oxide, 0.05% butylated hydroxytoluene, and 0.25% magnesium stearate. The subcoat was comprised of 95% hydroxyethyl cellulose and 5% polyethylene glycol. The semi permeable wall was comprised of 99% cellulose acetate of 39.8% acetyl content and 1% polyethylene glycol. The dosage form comprises two passageways, 25 mils (0.6 mm) on the center of the drug side.

EXAMPLE 4

Risiperidone Capsule Shaped Tablet, Trilayer 1 mg System

A dosage form adapted, designed and shaped as an osmotic drug delivery device was manufactured as follows: 188.0 g of poly(ethylene oxide) possessing a 200,000 molecular weight, and 10.0 g of hydroxypropylmethylcellulose comprising a 11,200 molecular weight were added to a Kitchenaid planetary mixing bowl. Next, the dry materials were mixed for approximately 1 minute. Then, 100 ml of denatured anhydrous alcohol was slowly added to the blended materials with continuous mixing for approximately 2 minutes. Next, the wet granulation was allowed to dry at room temperature over night, and then passed through a 10-mesh screen. Finally, 2.0 g of stearic acid was mixed into the granulation for 3 minutes.

Next, a drug granulation was prepared as follows: 6.6 g of risperidone, 181.4 g of poly(ethylene oxide) possessing a 200,000 molecular weight, and 10.0 g of hydroxpropylmethylcellulose comprising a 11,200 molecular weight were added to a Kitchenaid planetary mixing bowl. Next, the dry materials were mixed for approximately 1 minute. Then, 100 ml of denatured anhydrous alcohol was slowly added to the blended materials with continuous mixing for approximately 2 minutes. Next, the wet granulation was allowed to dry at room temperature over night, and then passed through a 10-mesh screen. Finally, 2.0 g of stearic acid was mixed into the granulation for 3 minutes.

Next, a push composition is prepared as follows: first, a binder solution was prepared. 7.80 kg of poly(vinylpyrrolidone) identified as K29-32 having an average molecular weight of 40,000 was dissolved in 52.2 kg of water. 26,000 g of sodium chloride and 1300 g of ferric oxide was sized using a Quadro Comil with a 21-mesh screen. Then, all the screened materials, and 95,810 g of pharmaceutically acceptable poly (ethylene oxide) comprising a 7,000,000 molecular weight were added to a Glatt Fluid Bed Granulator's bowl. The bowl was attached to the granulator and the granulation process was initiated for effecting granulation. Next, the dry powders were air suspended and mixed. Then, the binder solution was sprayed from 3 nozzles onto the powder. The granulating conditions were monitored during the process as follows: total solution spray rate of 700 g/min; inlet temperature 45 C; and process airflow of 500-5000 m3/hr. While spraying the binder solution, the filter bags were shaken for 10 seconds every 30 seconds to unglue any possible powder deposits. At the end of the solution spraying, 50,000 g, the coated granulated particles were continued with the drying process. The machine was turned off, and the coated granules were removed from the granulator. The coated granules were sized using a Fluid Air mill with a 6 mesh screen. The granulation was transferred to a Tote Tumbler, mixed with 65 g of butylated hydroxytoluene and lubricated with 325 g stearic acid.

Next, the placebo composition, the drug composition and the push composition were compressed into trilayer tablets on the Carver Tablet Press into a 3/16" (0.476 cm) diameter deep concave longitudinal layered arrangement. First, 70 mg of the placebo composition was added to the die cavity and pre-compressed, then 30 mg of the drug composition was added to the cavity and pre-compressed. Finally, 130 mg of the push composition was added and the layers were pressed under a pressure head of approximately ¼ a metric ton.

The trilayered arrangements were coated with a subcoat layer. The wall forming composition comprises 70% hydroxypropyl cellulose having an average molecular weight of 60,000 and 30% poly(vinylpyrrolidone) identified as K29-32 having an average molecular weight of 40,000. The wall-forming composition was dissolved in ethanol to make a 6% solids solution. The wall-forming composition was sprayed onto and around the bilayers in a 12" Vector HiCoater.

The subcoated arrangements were coated with a semi-permeable wall. The wall forming composition comprised 99% cellulose acetate having a 39.8% acetyl content and 1% polyethylene glycol comprising a 3350 viscosity-average molecular weight. The wall-forming composition was dissolved in an acetone:water (95:5 wt:wt) cosolvent to make a 5% solids solution. The wall-forming composition was sprayed onto and around the subcoated arrangements in a 12" Vector HiCoater.

Next, one 30 mil (0.762 mm) exit passageway was drilled through the semi-permeable wall to connect the drug layer with the exterior of the dosage system. The residual solvent was removed by drying for 60 hours as 45 C. and 45% humidity. Next, the osmotic systems were dried for 4 hours at 45 C. to remove excess moisture. The dosage form produced by this manufacture provides 94.0% poly(ethylene oxide) possessing a 200,000 molecular weight, 5.0% hydroxypropylmethylcellulose comprising a 11,200 molecular weight, and 1.0% stearic acid. The drug composition comprised 3.3% risperidone, 90.7% poly(ethylene oxide) possessing a 200,000 molecular weight, 5.0% hydroxpropylmethylcellulose comprising a 11,200 molecular weight, and 1.0% stearic acid. The push composition comprised 73.7% poly(ethylene oxide) comprising a 7,000,000 molecular weight, 20% sodium chloride, 5% poly(vinylpyrrolidone) identified as K29-32 having an average molecular weight of 40,000, 1.0% ferric oxide, 0.05% butylated hydroxytoluene, and 0.25% stearic acid. The subcoat wall comprises 70% hydroxypropyl cellulose having an average molecular weight of 60,000 and 30% poly(vinylpyrrolidone) identified as K29-32 having an average molecular weight of 40,000. The semipermeable wall comprised 99 wt % cellulose acetate comprising a 39.8% acetyl content and 1% polyethylene glycol comprising a 3,350 viscosity-average molecular weight. The dosage form comprised one passageway, 30 mils (0.762 mm), and it had a maximum risperidone release rate of 0.108 mg/hr (ORChID set 4587).

EXAMPLE 5

Risiperidone Capsule Shaped Tablet, Trilayer 2 mg System

A dosage form adapted, designed and shaped as an osmotic drug delivery device was manufactured as follows: first, a binder solution is prepared. 600 g of hydroxypropylmethylcellulose comprising a 11,200 molecular weight was dissolved in 5,400 g of water. 2,000 g of sodium chloride was screened with a 21-mesh screen. For the first drug granulation, 7,340 g of poly(ethylene oxide) possessing a 200,000 molecular weight, 2,000 g of screened sodium chloride and 300 g of hydroxpropylmethylcellulose comprising a 11,200 molecular weight were added to a Freund Fluid Bed Granulator's bowl. The bowl was attached to the granulator and the granulation process was initiated for effecting granulation. Next, the dry powders were air suspended and mixed. Then, the binder solution was sprayed from two nozzles onto the powder. The granulating conditions were monitored during the process as follows: total solution spray rate of 80 ml/min, an exhaust temperature of approximately 22 C and airflow of 200-300 cfm. While spraying the binder solution, the filter bags were shaken for 10 seconds after every 30 seconds spray cycle to unglue any possible powder deposits. 250 g of binder solution was sprayed onto the in materials the granulator and the granulation process was paused. 136.5 g of risperidone was then added into the granulator bowl. The granulation process was then continued using the same processing conditions. At the end of the solution spraying, 2000 g, the coated granulated particles were continued with the drying process. The machine was turned off, and the coated granules were removed from the granulator. The coated granules were passed through a 7 mesh screen. Finally, the dried and screened granulation were transferred to an appropriate container, mixed and lubricated with 99.4 g of stearic acid and 5.0 g of butylated hydroxytoluene for 10 minutes.

For the second drug granulation, 9,085 g of poly(ethylene oxide) possessing a 200,000 molecular weight, and 300 g of hydroxpropylmethylcellulose comprising a 11,200 molecular weight were added to a Freund Fluid Bed Granulator's bowl. The bowl was attached to the granulator and the granulation process was initiated for effecting granulation. Next, the dry powders were air suspended and mixed. Then, the binder solution was sprayed from two nozzles onto the powder. The granulating conditions were monitored during the process as follows: total solution spray rate of 80 ml/min, an exhaust temperature of approximately 23 C and airflow of 200-300 cfm.

While spraying the binder solution, the filter bags were shaken for 10 seconds after every 30 seconds spray cycle to unglue any possible powder deposits. 250 g of binder solution was sprayed onto the materials in the granulator and the granulation process was paused. 325.5 g of risperidone was then added into the granulator bowl. The granulation process was then continued using the same processing conditions. At the end of the solution spraying, 2000 g, the coated granulated particles were continued with the drying process. The machine was turned off, and the coated granules were removed from the granulator. The coated granules were passed through a 7 mesh screen. Finally, the dried and screened granulation were transferred to an appropriate container, mixed and lubricated with 94.1 g of stearic acid and 4.7 g of butylated hydroxytoluene for 10 minutes.

Next, a push composition was prepared as follows: first, a binder solution is prepared. 7.80 kg of poly(vinylpyrrolidone) identified as K29-32 having an average molecular weight of 40,000 was dissolved in 52.2 kg of water. 26,000 g of sodium chloride and 1300 g of ferric oxide was sized using a Quadro Comil with a 21-mesh screen. Then, all the screened materials, and 95,810 g of pharmaceutically acceptable poly(ethylene oxide) comprising a 7,000,000 molecular weight were added to a Glatt Fluid Bed Granulator's bowl. The bowl was attached to the granulator and the granulation process was initiated for effecting granulation. Next, the dry powders were air suspended and mixed. Then, the binder solution was sprayed from 3 nozzles onto the powder. The granulating conditions were monitored during the process as follows: total solution spray rate of 700 g/min; inlet temperature 45 C; and process airflow of 500-5000 m3/hr.

While spraying the binder solution, the filter bags were shaken for 10 seconds every 30 seconds to unglue any possible powder deposits. At the end of the solution spraying, 50,000 g, the coated granulated particles were continued with the drying process. The machine was turned off, and the coated granules were removed from the granulator. The coated granules were sized using a Fluid Air mill with a 6 mesh screen. The granulation was transferred to a Tote Tumbler, mixed with 65 g of butylated hydroxytoluene and lubricated with 325 g stearic acid.

Next, the two drug composition and the push composition were compressed into trilayer tablets on the Korsch Multilayer Tablet Press into a ³⁄₁₆" (0.476 cm) diameter deep concave longitudinal layered arrangement. First, 50 mg of the first drug composition was added to the die cavity and pre-compressed using a 100N force, then 40 mg of the second drug composition was added to the cavity and pre-compressed using a 100N force. Finally, 110 mg of the push composition was added and the layers are pressed under a pressure head of approximately 2000N.

The trilayered arrangements were coated with a subcoat layer. The wall forming composition comprises 70% hydroxypropyl cellulose having an average molecular weight of 60,000 and 30% poly(vinylpyrrolidone) identified as K29-32 having an average molecular weight of 40,000. The wall-forming composition was dissolved in ethanol to make a 8% solids solution. The wall-forming composition was sprayed onto and around the bilayers in a 24" Vector HiCoater.

The subcoated arrangements were coated with a semi-permeable wall. The wall forming composition comprises 99% cellulose acetate having a 39.8% acetyl content and 1% polyethylene glycol comprising a 3350 viscosity-average molecular weight. The wall-forming composition was dissolved in an acetone:water (95:5 wt:wt) cosolvent to make a 5% solids solution. The wall-forming composition was sprayed onto and around the subcoated arrangements in a 24" Vector HiCoater.

Next, two 30 mil (0.762 mm) exit passageway were drilled through the semi-permeable wall to connect the drug layer with the exterior of the dosage system. The residual solvent was removed by drying for 72 hours as 45 C and 45% humidity. Next, the osmotic systems were dried for 4 hours at 45 C. to remove excess moisture.

The dosage form produced by this manufacture provides a first drug composition that comprises 1.3% risperidone, 72.8% poly(ethylene oxide) possessing a 200,000 molecular weight, 19.9% sodium chloride, 5.0% hydroxpropylmethylcellulose comprising a 11,200 molecular weight, 1.0% stearic acid, and 0.05% butylated hydroxytoluene. The second drug composition comprises 3.1% risperidone, 90.85% poly(ethylene oxide) possessing a 200,000 molecular weight, 5.0% hydroxypropylmethylcellulose comprising a 11,200 molecular weight, 1.0% stearic acid and 0.05% butylated hydroxytoluene. The push composition comprised 73.7% poly(ethylene oxide) comprising a 7,000,000 molecular weight, 20% sodium chloride, 5% poly(vinylpyrrolidone) identified as K29-32 having an average molecular weight of 40,000, 1.0% ferric oxide, 0.05% butylated hydroxytoluene, and 0.25% stearic acid. The subcoat wall comprised 70% hydroxypropyl cellulose having an average molecular weight of 60,000 and 30% poly(vinylpyrrolidone) identified as K29-32 having an average molecular weight of 40,000. The semipermeable wall comprised 99 wt % cellulose acetate comprising a 39.8% acetyl content and 1% polyethylene glycol comprising a 3,350 viscosity-average molecular weight. The dosage form comprised two passageways, 30 mils (0.762 mm), and it had a maximum risperidone release rate of 0.176 mg/hr.

We claim:

1. A method for treating a subject in need of treatment comprising orally administering a once-a-day oral dosage form containing as an active agent a therapeutically effective amount of paliperidone or a pharmaceutically acceptable addition salts thereof wherein the dosage form comprises:
   (a) a core having three layers and a portion of the active agent is contained within a first drug composition layer and the remaining portion of the active agent is contained within a second drug composition layer, wherein the proportion of active agent contained within the first layer to the active agent contained within the second layer is less than about 0.33, wherein the first drug composition layer contains an osmagent and a second drug composition layer does not contain an osmagent and wherein a fluid-expandable polymer is contained within a third layer;
   (b) a subcoat surrounding said core;
   (c) a semipermeable membrane surrounding the core to form a compartment having an osmotic gradient to drive fluid from an external fluid environment contacting the semipermeable membrane into the compartment; and
   (d) an orifice formed through the semipermeable membrane and into the core to permit the active agent to be released from within the compartment into the external fluid environment wherein the first drug composition layer is proximal to the orifice;
   wherein the dosage form following oral administration to said subject releases the active agent at a substantially ascending release rate for at least 18 hours as determined by in vitro dissolution testing.

2. The method of claim 1 for administering an active agent to a subject wherein the core is a capsule shaped tablet.

3. The method according to claim 1 wherein the osmagent is sodium chloride salt.

4. The method according to claim 1 wherein a $C_{max}$ occurs after about 14 hours after administration to the subject.

5. The method according to claim 1 wherein a $C_{max}$ occurs between about 16 hours and about 22 hours after administration to the subject.

6. The method according to claim 1 wherein a $C_{max}$ occurs between about 18 hours and about 21 hours after administration to the subject.

7. The method according to claim 1 wherein the concentration of active agent in the first drug layer to the concentration of active agent in the second drug layer is less than 0.44.

8. A oral tablet dosage form comprising as an active agent a therapeutically effective amount of paliperidone or a pharmaceutically acceptable addition salts thereof wherein the dosage form comprises:
   (a) a core having three layers and a portion of the active agent is contained within a first drug composition layer and the remaining portion of the active agent is contained within a second drug composition layer, wherein the proportion of active agent contained within the first layer to the active agent contained within the second layer is less than about 0.33, wherein the first drug composition layer contains an osmagent and a second drug composition layer does not contain an osmagent and wherein a fluid-expandable polymer is contained within a third layer;
   (b) a subcoat surrounding said core;
   (c) a semipermeable membrane surrounding the core to form a compartment having an osmotic gradient to drive fluid from an external fluid environment contacting the semipermeable membrane into the compartment; and
   (d) an orifice formed through the semipermeable membrane and into the core to permit the active agent to be released from within the compartment into the external fluid environment wherein the first drug composition layer is proximal to the orifice;
   wherein the dosage form following oral administration to a subject releases the active agent from the dosage form at a substantially ascending release rate for at least 18 hours as determined by in vitro dissolution testing.

9. The dosage form of claim 8 characterized by releasing the active agent from the dosage form at a substantially ascending rate of release for about 18 hours to about 20 hours.

10. The dosage form of claim 8 characterized by having a $T_{90}$ from the core occurring at about 20 hours.

11. The dosage form according to claim 8 further comprising a subcoat for reducing the rate of degradation of the active agent paliperidone, which subcoat comprises a hydroxyalkylcellulose polymer possessing a 8,500 to 4,000,000 molecular weight that at least partially surrounds the core and is positioned between an inside surface of the semipermeable membrane and the core.

12. The dosage form according to claim 8 further comprising a subcoat for reducing the rate of degradation of the active agent pafiperidone which subcoat comprises a mixture of hydroxypropyl cellulose and providone prepared in ethanol that at least partially surrounds the core and is positioned between an inside surface of the semipermeable membrane and the core.

13. The method according to claim 1 wherein the first drug composition layer contains at least 20% an osmagent.

14. The dosage form according to claim 8 wherein the first drug composition layer contains at least 20% an osmagent.

* * * * *